US012629069B2

(12) United States Patent
Wiesemann

(10) Patent No.: US 12,629,069 B2
(45) Date of Patent: May 19, 2026

(54) APPARATUS AND METHOD FOR DRAWING BLOOD AND OTHER BODILY FLUIDS

(71) Applicant: Mediproducts Development, Inc., Newport Beach, CA (US)

(72) Inventor: Scot Albert Wiesemann, Newport Beach, CA (US)

( * ) Notice: Subject to any disclaimer, the term of this patent is extended or adjusted under 35 U.S.C. 154(b) by 853 days.

(21) Appl. No.: 17/658,810

(22) Filed: Apr. 11, 2022

(65) Prior Publication Data

US 2022/0322983 A1     Oct. 13, 2022

Related U.S. Application Data

(60) Provisional application No. 63/179,131, filed on Apr. 23, 2021, provisional application No. 63/173,215, filed on Apr. 9, 2021.

(51) Int. Cl.
*A61B 5/15*        (2006.01)
*A61B 5/153*       (2006.01)

(52) U.S. Cl.
CPC .. *A61B 5/150259* (2013.01); *A61B 5/150236* (2013.01); *A61B 5/153* (2013.01)

(58) Field of Classification Search
CPC ........ A61B 5/150259; A61B 5/150236; A61B 5/153; A61B 5/15003; A61B 5/150244; A61M 5/178; A61M 5/31; A61M 5/32
See application file for complete search history.

(56) References Cited

U.S. PATENT DOCUMENTS 4,216,782 A * 8/1980 Sarstedt ........... A61B 5/150389
600/577
6,030,366 A * 2/2000 Mitchell ............. A61M 5/3271
604/232

(Continued)

FOREIGN PATENT DOCUMENTS

WO      WO-2014025564 A1 * 2/2014 ............ A61M 5/178

OTHER PUBLICATIONS

Luke J. Haseler, Randy R. Sibbitt, Wilmer L. Sibbit JR., Adrian A. Michael, Charles M. Gasparovic and Arthur D. Bankhurst, Syringe and Needle Size, Syringe Type, Vacuum Generation, and Needle Control in Aspiration Procedures, Cardiovasc Intervent Radiol. Jun. 2011 ; 34(3): 590-600. doi:10.1007/s00270-010-0011-z, National Institutes of Health, United States.

Primary Examiner — Eric J Messersmith
Assistant Examiner — Nidhi N Patel
(74) Attorney, Agent, or Firm — CIONCA IP Law P.C.

(57)        ABSTRACT

An adapter for a syringe having a barrel, a pair of syringe flanges secured to the barrel, and a plunger with a plunger top, the plunger being slidably disposed within the barrel, the adapter having a barrel guide configured to movably surround the barrel, a plunger lock configured to secure the plunger to the adapter, a support body disposed between and associated with the barrel guide and the plunger lock and a front grip associated with the barrel guide. By compressing the syringe flanges and the front grip toward each other, the barrel may travel forward through the barrel guide, thus drawing fluid into the syringe. The adapter, by allowing a compression force to be used to draw a fluid into the syringe, allows an individual to quickly and easily perform a blood draw or other fluid drawing operation with one hand, removing the need for a second user.

10 Claims, 16 Drawing Sheets

(56)                    References Cited

U.S. PATENT DOCUMENTS

2015/0148749 A1*  5/2015  Cohn ................. A61M 5/3243
                                                                          604/198
2021/0038820 A1*  2/2021  Alsuhaibani ........ A61M 5/3148

* cited by examiner

APPARATUS AND METHOD FOR DRAWING BLOOD AND OTHER BODILY FLUIDS

CROSS-REFERENCE TO RELATED APPLICATIONS

This application is a Non-Provisional Application and claims the benefit of U.S. Provisional Application No. 63/173,215, filed on Apr. 9, 2021, and U.S. Provisional Application No. 63/179,131, filed on Apr. 23, 2021, both of which are hereby incorporated by reference, to the extent that they are not conflicting with the present application.

BACKGROUND OF INVENTION

1. Field of the Invention

The invention relates generally to methods and apparatuses for drawing blood or other fluids from the human body, and more specifically to methods and apparatuses for drawing blood or other liquids from the human body without the need for assistance from a secondary user.

2. Description of the Related Art

As is known, drawing blood is a very commonplace procedure of great importance for allowing doctors, laboratory technicians, and the like the ability to conduct tests, collect blood donations for transfusions, and perform a wide variety of treatments. Typically, blood is drawn from the body (e.g., from veins in the wrist, arm, inner elbow, etc.) using syringes. These syringes are conventionally provided with vials or barrels (e.g., plastic or glass vials) of varying sizes, and typically have a pre-loaded vacuum disposed within the vials, such that during a blood draw, once the rubber topper of the syringe penetrates the vacuum, blood is drawn more easily into the vial by function of the pre-loaded vacuum. With smaller syringes, for example, (i.e., syringes having vials that can accommodate less than 20 milliliters (ML) of blood), the blood drawing process can be performed on a patient easily by a nurse, doctor, care provider, or other authorized user. With larger syringes, where blood draws of 20 ML to well over 50 ML are to be performed, a secondary user, such as a second nurse, phlebotomist, doctor, etc., is often needed to assist the primary user with the blood drawing process.

As an example, during the blood drawing process, the primary user (nurse, doctor, care provider) pulls the syringe plunger backwardly (i.e., toward themselves) with one hand, such that to draw blood or other liquid into the vial/barrel of the syringe, while applying pressure to the entry point of the tubing/butterfly/needle entering the patient's vein. This applying of pressure to the entry point ensures that the needle in the patient's vein does not move around during the blood draw, which would cause pain for the patient. For larger draws (20 ML or more), for example, where the vial/barrel of the syringe is physically larger/longer, as the primary user draws the patient's blood (or other fluid), friction, blood thickness, increased vacuum capacity, etc. may hinder and thus strain the primary user's ability to easily and effectively draw blood by themselves with just a single hand. As such, for large blood draws, a secondary user, such as a second nurse/phlebotomist/care provider (i.e., "a third hand"), is often needed to hold down the entry point, while the primary user uses both hands to pull on the plunger to draw blood into the larger vial.

Because a second user is needed for larger blood draws using conventional syringes, the blood drawing process may be inefficient and time-consuming for the second user who may be utilizing their time and effort elsewhere (conducting another blood draw, for example). Typical medical procedures, including veterinary procedures, that involve large fluid draws (20 ML or more), for example, include platelet-rich plasma (PRP) therapy, phlebotomy, amniocentesis, seroma/hematoma drainage (post-surgery, injury), joint aspiration (infection, arthritis, injury), thoracentesis, paracentesis, abscess/wound drainage, cyst aspiration, suprapubic bladder aspiration, among others. As such, there is much room for improvement for a wide variety of medical procedures and fields requiring large fluid draws.

Therefore, there is a need to solve the problems described above by providing an apparatus and method for effectively, efficiently, and safely drawing blood or another fluid without the need for a third hand.

The aspects or the problems and the associated solutions presented in this section could be or could have been pursued; they are not necessarily approaches that have been previously conceived or pursued. Therefore, unless otherwise indicated, it should not be assumed that any of the approaches presented in this section qualify as prior art merely by virtue of their presence in this section of the application.

BRIEF INVENTION SUMMARY

This Summary is provided to introduce a selection of concepts in a simplified form that are further described below in the Detailed Description.

In an aspect, an adapter for a syringe having a barrel, a pair of syringe flanges secured to the barrel, and a plunger with a plunger top, the plunger being slidably disposed within the barrel is provided, the adapter comprising: a first end and a second end; a barrel guide disposed at the first end, the barrel guide being configured to movably surround the barrel; a plurality of alignment fins and alignment plates disposed within the barrel guide; a first plate and a second plate disposed at the second end of the adapter, wherein the first and second plates are configured to secure the plunger top to the adapter; a medial body disposed between and associated with the first end and the second end, the medial body being comprised of a first half and a second half, wherein the first half and the second half are associated with each other by hinges; an adapter lock configured to secure the first half and second half of the medial body together to surround the syringe within the adapter; and a pair of adapter flanges associated with the barrel guide; wherein application of a force to move the pair of syringe flanges toward the barrel guide is configured to cause the barrel to traverse forward through the barrel guide, thus causing a fluid to be drawn into the barrel. Thus, an advantage of the disclosed adapter is that a "third hand" is no longer needed to draw a fluid into a syringe, allowing for a more effective and time-efficient fluid drawing process. An additional advantage is that the time spent by the third hand (i.e., the secondary user) for the blood drawing process may now be utilized to attend to other matters. Another advantage is that pain incurred from the unintentional moving of a needle in a patient's vein may be avoided through the use of the barrel guide in conjunction with the alignment fins and alignment plates. Another advantage is that unwanted leaking or spilling from the syringe barrel may be prevented, such that the drawn blood or other liquids may be maintained for further use. An additional advantage is the ease and simplicity of the assembly and disassembly of the disclosed adapter, allowing for quick and efficient replacement of apparatus components. Another advantage of the above-described apparatus is the ability to accommodate syringes of varying lengths and/or size.

In another aspect, an adapter for a syringe having a barrel, a pair of syringe flanges secured to the barrel, and a plunger with a plunger top, the plunger being slidably disposed within the barrel is provided, the adapter comprising: a barrel guide configured to movably surround the barrel; a plunger lock configured to secure the plunger top to the adapter to prevent movement of the plunger; a medial body disposed between and associated with the barrel guide and the plunger lock, the medial body being comprised of a first half and a second half being configured to associate with each other, to surround the syringe; and a pair of adapter flanges disposed on the medial body; wherein application of a force to move the pair of syringe flanges toward the barrel guide is configured to cause the barrel to traverse forward through the barrel guide, thus causing a fluid to be drawn into the barrel. Again, an advantage of the disclosed adapter is that a "third hand" is no longer needed to draw a fluid into a syringe, allowing for a more effective and time-efficient fluid drawing process. An additional advantage is that the time spent by the third hand (i.e., the secondary user) for the blood drawing process may now be utilized to attend to other matters. Another advantage is that pain incurred from the unintentional moving of a needle in a patient's vein may be avoided through the use of the barrel guide. Another advantage is that unwanted leaking or spilling from the syringe barrel may be prevented, such that the drawn blood or other liquids may be maintained for further use. An additional advantage is the ease and simplicity of the assembly and disassembly of the disclosed adapter, allowing for quick and efficient replacement of apparatus components. Another advantage of the above-described apparatus is the ability to accommodate syringes of varying lengths and/or size.

In another aspect, an adapter for a syringe having a barrel, a pair of syringe flanges secured to the barrel, and a plunger with a plunger top, the plunger being slidably disposed within the barrel is provided, the adapter comprising: a barrel guide configured to movably surround the barrel; a plunger lock configured to secure the plunger to the adapter; a support body disposed between and associated with the barrel guide and the plunger lock; and a front grip associated with the barrel guide; wherein application of a force to move the pair of syringe flanges toward the barrel guide is configured to cause the barrel to traverse forward through the barrel guide, thus causing a fluid to be drawn into the barrel. Again, an advantage of the disclosed adapter is that a "third hand" is no longer needed to draw a fluid into a syringe, allowing for a more effective and time-efficient fluid drawing process. An additional advantage is that the time spent by the third hand (i.e., the secondary user) for the blood drawing process may now be utilized to attend to other matters. Another advantage is that pain incurred from the unintentional moving of a needle in a patient's vein may be avoided through the use of the barrel guide. Another advantage is that unwanted leaking or spilling from the syringe barrel may be prevented, such that the drawn blood or other liquids may be maintained for further use. An additional advantage is the ease and simplicity of the assembly and disassembly of the disclosed adapter, allowing for quick and efficient replacement of apparatus components. Another advantage of the above-described apparatus is the ability to accommodate syringes of varying lengths and/or size.

The above aspects or examples and advantages, as well as other aspects or examples and advantages, will become apparent from the ensuing description and accompanying drawings.

BRIEF DESCRIPTION OF THE DRAWINGS

For exemplification purposes, and not for limitation purposes, aspects, embodiments or examples of the invention are illustrated in the figures of the accompanying drawings, in which.

DETAILED DESCRIPTION

Figure 1A:
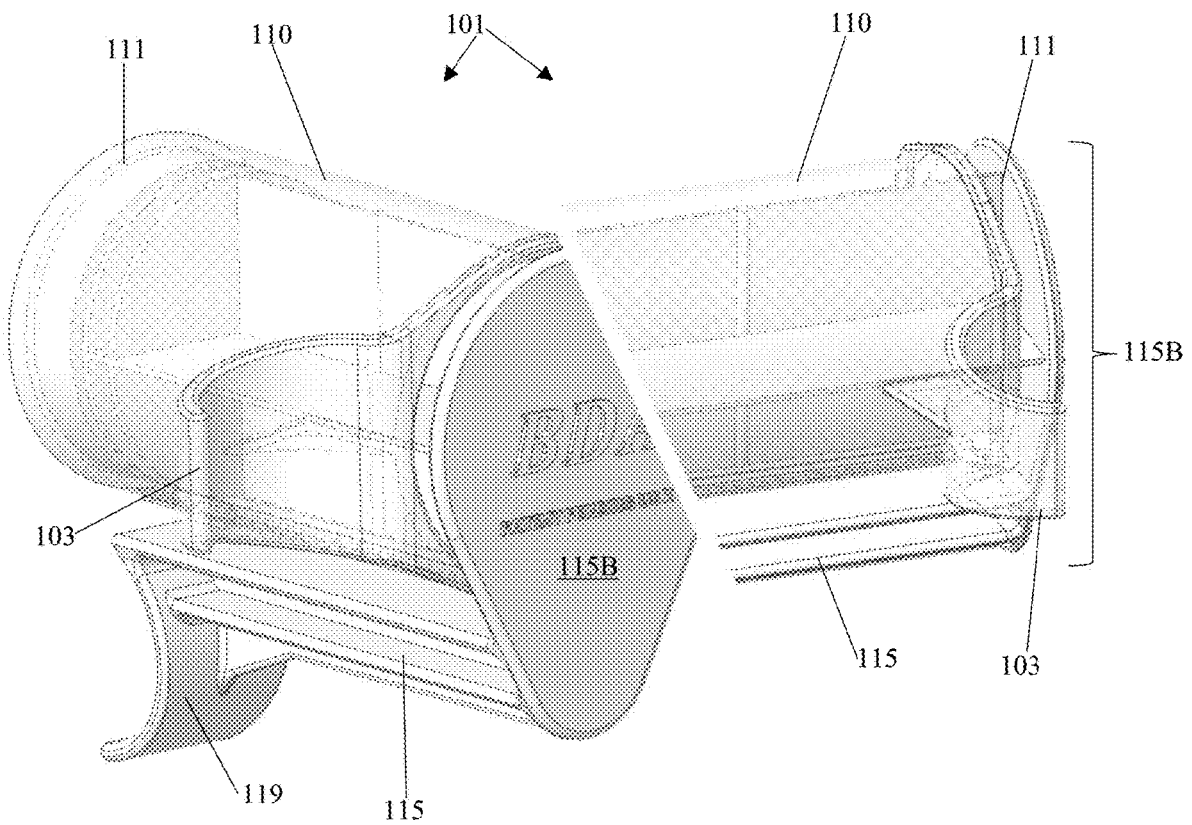
FIGS. 1A-C illustrate a perspective view, and side elevation views, of a compact blood drawing apparatus, in an open state and in a closed state, respectively, according to an aspect.

What follows is a description of various aspects, embodiments and/or examples in which the invention may be practiced. Reference will be made to the attached drawings, and the information included in the drawings is part of this detailed description. The aspects, embodiments and/or examples described herein are presented for exemplification purposes, and not for limitation purposes. It should be understood that structural and/or logical modifications could be made by someone of ordinary skills in the art without departing from the scope of the invention.

It should be understood that, for clarity of the drawings and of the specification, some or all details about some structural components or steps that are known in the art are not shown or described if they are not necessary for the invention to be understood by one of ordinary skills in the art.

For the following description, it can be assumed that most correspondingly labeled elements across the figures (e.g., 110 and 210, etc.) possess the same characteristics and are subject to the same structure and function. If there is a difference between correspondingly labeled elements that is not pointed out, and this difference results in a non-corresponding structure or function of an element for a particular embodiment, example or aspect, then the conflicting description given for that particular embodiment, example or aspect shall govern.

Figure 1B:
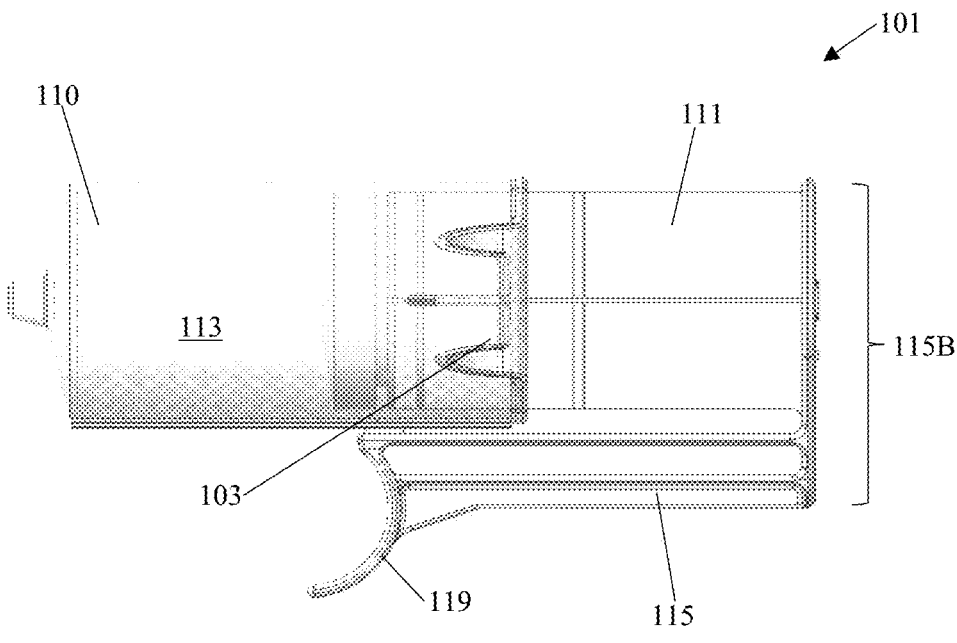
Figure 1C:
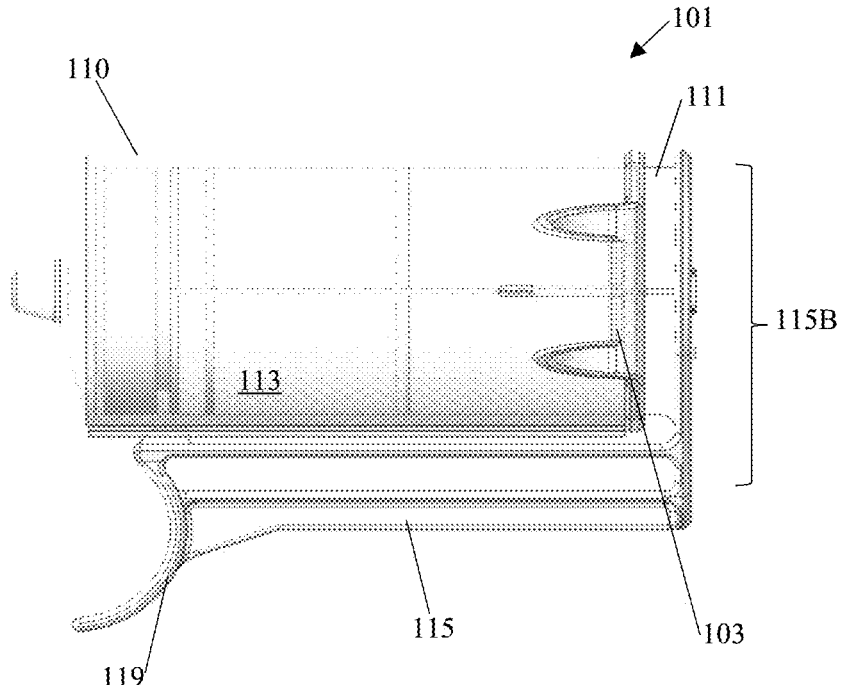

FIGS. 1A-1C illustrate a perspective view, and side elevation views, of a compact blood drawing apparatus 101, in an open state and in a closed state, respectively, according to an aspect. As described throughout the Background above, blood and other bodily liquids may be drawn from the body, as needed, conventionally using a syringe having a needle and a vial/barrel, for example. Like a vacuum, the syringe primarily uses a suction method, induced by the pull of the top of the plunger, for example, to pull/draw blood and other liquids into the barrel of the syringe, as an example. For larger syringes having larger barrels, the ability to effectively and easily pull the base of the plunger, such that to draw blood into the barrel, becomes much more difficult, as described previously above, and often times thus requires the assistance of a third hand (e.g., the hand of a secondary user). As will be described throughout this disclosure below, an apparatus and a method of using said apparatus may negate the need for such a third hand, thus enabling the more efficient and effective drawing of larger amounts of blood and other liquids.

As shown in FIGS. 1A-1B, the blood drawing apparatus ("blood drawing apparatus," "apparatus," "blood draw assembly", "fluid drawing apparatus", "apparatus") 101 may be provided in a first embodiment as a compact device, as an example. As an example, the compact apparatus 101 may comprise a syringe portion ("syringe portion," "syringe") 110 and an attachment 115 having a first end (not shown) ("front end") and second end 115B ("rear end", "back end"), as shown, which will be described in more detail throughout this disclosure below. As shown, the syringe 110 may be provided with a plunger 111 and a flange 103 ("shoulder"), as is commonly provided for traditional syringes. As shown in FIG. 1, the attachment 115 may also be provided with a flange/trigger ("attachment flange", "attachment trigger", "adapter flange") 119, for example, which will be described in greater detail later. As an example, the syringe flange 103 and the attachment flange 119 may each be adapted to receive a finger of a user (e.g., nurse, phlebotomist, care provider, doctor, etc.) for causing a sliding of the barrel 113, and thus, the drawing of blood into the syringe barrel, which will be discussed in more detail below. It should be understood that the attachment 115 may be referred to as an "adapter" 115, as a result of said attachment's ability to be slidably fitted around a syringe 110 to allow a compressive force exerted between the syringe 110 and the outer attachment 115 to draw a fluid into said syringe 110.

As shown in FIGS. 1B-1C, the syringe 110 of the compact apparatus 101 may further comprise a barrel 113 adapted to be filled with blood or other bodily fluids, for example. As an example, for the compact embodiment shown, the barrel 113 may be approximately 2 inches long, and may be adapted to hold up to 60 ML of fluid, for example. As shown in FIG. 1C, the compact apparatus 101 may initially be provided in a closed state, and via the user applying pressure (via index finger and thumb, respectively, for example) to the attachment trigger 119 and the syringe flange 103, the barrel 113 of the syringe 110 may be traversed forward to an open state, as shown in FIG. 1B, such that to fill the barrel 113 with blood or other bodily fluids, for example. As will be described throughout this disclosure below, the apparatus 101 may be provided in additional embodiments, each adapted to draw blood or other bodily fluids into a 60 ML syringe, for example.

Figure 2:
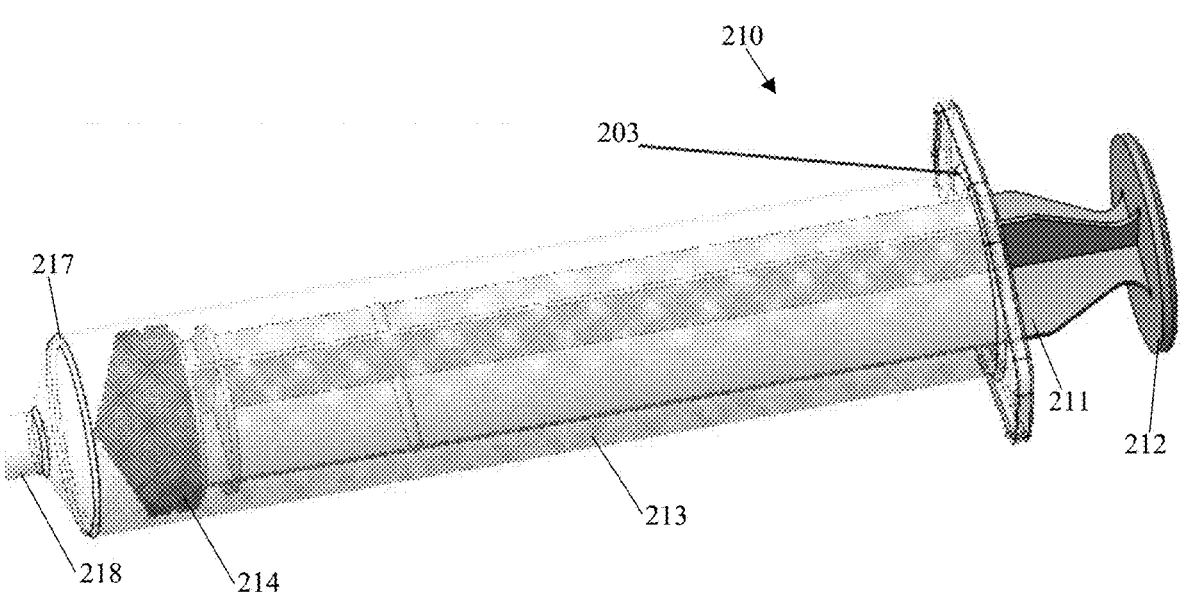
FIG. 2 illustrates a perspective view of a syringe of a blood drawing apparatus, according to an aspect.

FIG. 2 illustrates a perspective view of a syringe 210 of a blood drawing apparatus (not shown), according to an aspect. As mentioned previously above when referring to FIG. 1, the blood drawing apparatus (e.g., 101) may comprise a central syringe 210 and an outer attachment or adapter slidably surrounding said syringe 210. As shown in FIG. 2, the central syringe 210 may be provided with a plunger 211, shown previously in FIG. 1, and a flange 203 protruding outwardly on either side of the syringe 210. As an example, the syringe 210 may comprise a barrel/vial 213 connected above the flange 203; the barrel 213 may be cylindrical in shape, as shown, and may thus have a diameter. As an example, the barrel 213 may be offset from the flange 203 by 0.070 inches, for example, such that to provide the outer attachment (not shown) an adequate surface area on which to abut the syringe 210, as will be described in more detail later.

As shown in FIG. 2, the syringe 210 may further comprise a shaft end 217 connected to a hub or adapter 218, as an example. The hub 218 may be adapted to receive a needle hub and needle, for example, for insertion into and thus association with a vein (or other body part) for the drawing of blood (or other liquids), as an example. Finally, as shown in FIG. 2, the plunger 211 may comprise a top ("plunger top") 212 and a seal ("plunger seal") 214 disposed at an opposite end of the plunger 211, for example. As an example, the plunger seal 214 may be made of rubber or other frictional materials. As is known, the plunger seal 214 creates a vacuum within the barrel 213, such that as the plunger top 212 is drawn backwardly (toward the user), blood (or other liquids) are caused to be drawn into the barrel 213, such that to gradually fill the barrel 213 as desired. However, as described previously above, in the case of larger syringes and larger barrels, the pulling of the plunger and the creation of a larger vacuum becomes much more difficult, thus requiring the assistance of the third hand. As will be described in detail below, the syringe 210 may be provided with an outer attachment or adapter, such as outer attachment 315 of FIG. 3, for enabling a single user to draw blood without the need for assistance from an additional third hand.

The structure of the syringe 210 may be simplified in order to emphasize elements that interact more directly with the elements of the herein disclosed adapter, such as adapter 101 of FIG. 1A. The syringe 210 may be described as having a barrel 213, a pair of syringe flanges 203 secured to the barrel 213, and a plunger 211 with a plunger top 212, the plunger 211 being slidably disposed within the barrel 213. As will be described in greater detail hereinbelow, the plunger 211 may be secured to the adapter, such that only the barrel 213 and the attached syringe flanges 203 are permitted to move slidably.

It should be understood that the syringe and its exemplary components may be made of any suitably durable and cost-effective material. For example, the barrel may be constructed of a transparent plastic material or glass, and the plunger 211 and the connected plunger top 212 may be constructed of a plastic material as well. It should be understood that the barrel 213 may be provided with a scale, as is commonly provided, for measuring an amount of a liquid being drawn into the barrel 213, as an example.

Figure 3:
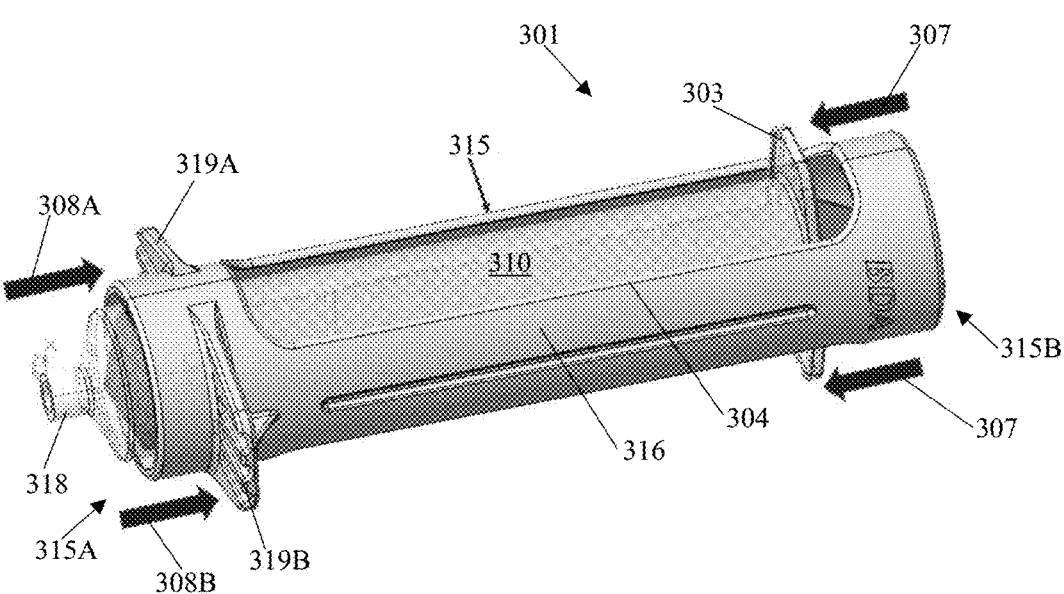
FIG. 3 illustrates a perspective view of a blood drawing apparatus, in a closed state, according to an aspect.

FIG. 3 illustrates a perspective view of a blood drawing apparatus 301, in a closed state, according to an aspect. As described throughout this disclosure above, a syringe alone may be inadequate when attempting to draw large amounts of blood (20 ML or more) without the need for help from a third hand, for example, due to the increased difficulty of pulling the plunger top (e.g., 212 in FIG. 2). As will be described in detail below, the syringe may be provided with an encasing outer attachment ("adapter," "blood draw assist attachment," "BDA attachment", "draw assist attachment"), such as outer attachment 315 of FIG. 3, for simplifying and making the blood drawing process more effective.

As shown in FIG. 3, the syringe 310, described previously when referring to FIG. 2 above, may be encased or slidably surrounded by the blood draw assist attachment 315, which is adapted to slidably surround the barrel (e.g., 213 in FIG. 2) of the syringe 310. As an example, the BDA attachment 315 may comprise a first end 315A and an opposite second end 315B, as shown, and a medial portion or body 316 extending between and associated with the first and the second ends 315A and 315B. As will be described in greater detail later, the medial body 316 may comprise an inner frame 304 along which the syringe flange 303 may slide, as an example. It should be understood that the medial body 316 may comprise two oppositely disposed inner frames 304 to accommodate both syringe flanges 303, for example. Additionally, as shown in FIG. 3, the BDA attachment 315 may be provided with a pair of attachment flanges ("attachment flanges," "BDA flanges" "adapter flanges") 319A and 319B, as discussed similarly when referring to FIG. 1 above. As shown, the BDA flanges 319A and 319B may be disposed near the first end 315A and may each be provided with a plurality of circular grooves, for example, for creating a frictional/gripping surface in each of the BDA flanges 319A and 319B.

As mentioned throughout this disclosure above, the BDA attachment 315 may encase/slidably surround the syringe 310, as shown in FIG. 3. As an example, when attached around the syringe 310, the first end 315A of the BDA attachment 315 may interlock around the barrel of the syringe 310 near the shaft end (e.g., 217 in FIG. 2), and the second end 315B may interlock around the plunger top (e.g., 212 in FIG. 2), which will be discussed in more detail when referring to FIG. 8, for example. Thus, as will be described in more detail throughout this disclosure below, the plunger top, such as plunger top 212 of FIG. 2, may be kept fixed and secured within the BDA attachment 315, such that the plunger top is prevented from moving. As shown in FIG. 3, the BDA flanges 319A and 319B and the syringe flanges 303 may each be adapted to receive an exertion/compression force, as indicated by the arrows. As an example, as indicated by arrows 308A and 308B, the BDA flanges 319A and 319B, respectively, may be adapted to receive two fingers (e.g., index finger and middle finger), the two fingers applying the frontal exertion forces indicated by 308A and 308B, respectively. Similarly, as an example, as indicated by arrows 307, the syringe flange 303 may be adapted to receive at least one finger (e.g., thumb), the at least one finger applying the rear exertion force indicated by 307. As will be described in detail below, the front and rear exertion forces may cause the syringe barrel 313 to slidably traverse within the BDA attachment 315, which may cause the drawing of blood (or other liquids) in through the syringe hub 318, as an example.

Figures 4, 5:
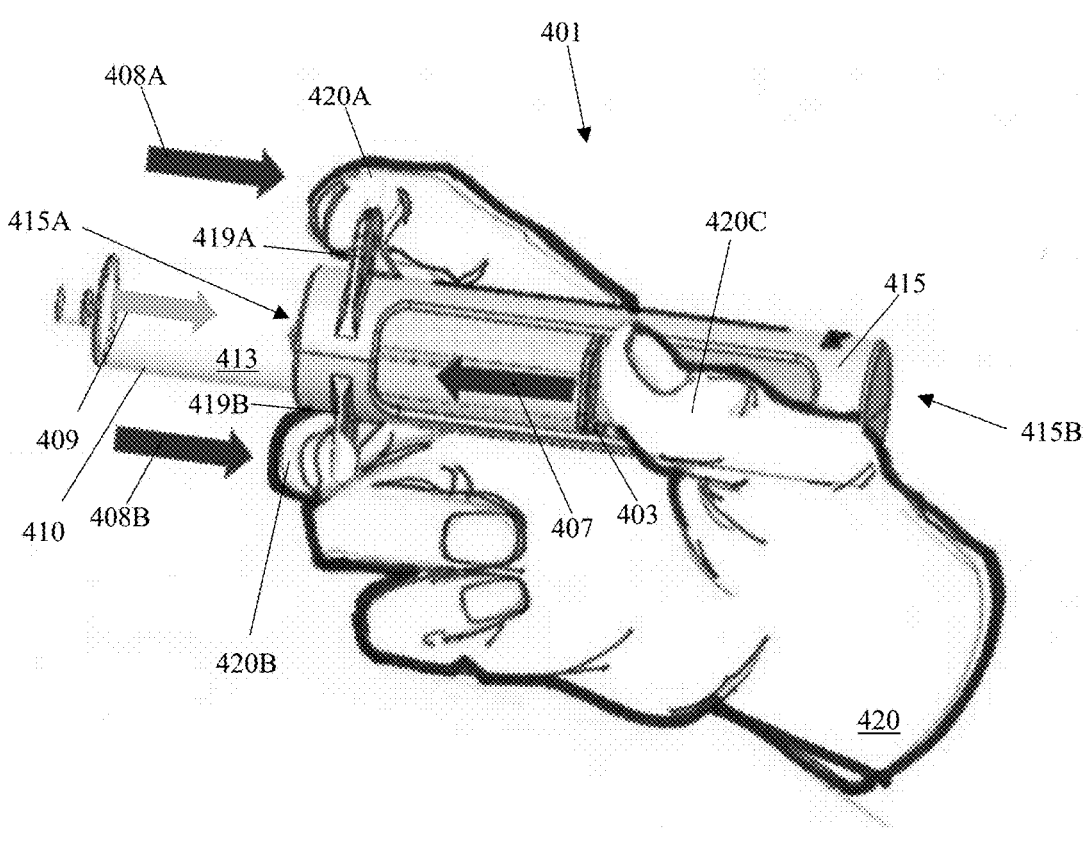
FIG. 4 is a diagram illustrating a perspective view of an example of use of the blood drawing apparatus of FIG. 3, according to an aspect.
FIG. 5 illustrates alternating side elevation views of the blood drawing apparatus, in a closed state, according to an aspect.

FIG. 4 is a diagram illustrating a perspective view of an example of use of the blood drawing apparatus 301 of FIG. 3, according to an aspect. As mentioned previously above when referring to FIG. 3, the apparatus 401 may comprise the syringe 410 and a surrounding BDA attachment 415. As described in the Background hereinabove, traditionally, syringes operate as vacuums configured to draw blood into the syringe barrel by a pulling of the plunger backwardly toward the user. As will be described in detail below, the apparatus 401 essentially reverses the motion of travel of the plunger, such that the plunger is no longer pulled backwardly to cause a drawing of blood into the syringe barrel, as an example.

As described previously above when referring to FIG. 3, the BDA attachment flanges 419A, 419B, and the syringe flanges 403, may each be adapted to receive an exertion/compression force induced by a finger of a user 420. As an example, the BDA flanges 419A and 419B may be adapted to receive the index finger and the middle finger, respectively, of the user 420, as indicated. Additionally, the flange 403 of the syringe 410 may be adapted to receive the thumb of the user 420, as indicated. It should be understood that, as shown in FIG. 4 for this example, only a single hand of the user 420 is being used. As indicated, the index finger 420A and the middle finger 420B of the user 420 may apply frontal exertion forces 408A and 408B onto the BDA flanges 419A and 419B, respectively (e.g., a force being applied in the direction of the second end 415B from the first end 415A, a force being applied to the BDA flanges 419A, 419B attempting to move them toward the second end 415B), while the thumb 420C applies a rear exertion force 407 onto the syringe flange 403 (e.g., a force being applied in the direction of the first end 415A from the second end 415B, a force being applied to the syringe flange 403 attempting to move it toward the first end 415A), as similarly mentioned previously above. As mentioned previously above when referring to FIG. 3, the plunger top (e.g., 212 in FIG. 2) may be fixed within the BDA attachment 415, such that the plunger is prevented from moving during blood draw. As such, as the front and rear exertion forces 408A, 408B and 407, respectively, are applied to the apparatus 401, the barrel 413 of the syringe 410 is caused to traverse forwards (in the same direction as 407, for example), while the plunger is kept secured to the BDA attachment 415. In this way, blood (or other liquids) are drawn into the barrel 413, in the direction of arrow 409, for example, as shown, as the syringe flange 403 is compressed toward the BDA flanges 419A and 419B.

It should be understood that the described forces being exerted upon the BDA flanges 419A, 419B and the syringe flanges 403 may only result in the movement of the barrel 413 and the syringe flanges 403 toward the first end 415A, as the BDA attachment 415 and its associated BDA flanges 419A, 419B may be kept stationary during drawing. As such, the plunger (not shown) may also remain stationary with respect to the BDA attachment 415, as a result of the plunger top being secured within the BDA attachment 415. The resultant "compressive force" produced by the frontal exertion forces 408A, 408B exerted on the BDA flanges 419A, 419B and the rear exertion force 407 exerted on the syringe flange 403 may be described in various ways, including but not limited to, exerting a compression force "between", "on", "simultaneously to", etc., the BDA flanges 419A, 419B and the syringe flange 403. The same action may be described as applying a force to move the pair of syringe flanges 403 toward a barrel guide, such as guiding collar 851 of FIG. 8, the first end 415A or the BDA flanges 419A, 419B. As described herein, regardless of how this action/force is depicted or described, said action/force results in the traversing of the barrel 413 through the first end 415A/barrel guide to allow for drawing of a fluid into the syringe 410, and thus each description should be understood to be equivalent and interchangeable.

As outlined above, the BDA attachment 415 may thus enable a single user to draw blood or liquid into the syringe barrel 413, due to the reversal of direction of induced forces. For example, as described throughout this disclosure above, traditional syringes require a pulling force to be applied to the plunger top to draw blood into the barrel. However, for larger syringes, a greater pulling force is required, and may thus require two hands to pull on the plunger top, while a third hand holds down the needle entry point in the vein (or other body part). As shown in FIG. 4, the BDA attachment 415 replaces the traditional pulling force with a compression force (oppositely facing arrows 408A, 408B and 407), such that the user pushes with their thumb as opposed to pulling with their thumb. As can be visualized, the strength of the pushing force of a thumb is naturally stronger than the pulling force of a thumb (due to the added assistance from the hand and wrist muscles, for example, in the compression direction). Thus, even for bigger syringes and larger blood draws, the pushing force exerted by the thumb may be more than sufficient to effectively draw blood into the barrel, as needed. Thus, an advantage of the disclosed apparatus is that the third hand is no longer needed, allowing for a more effective and time-efficient blood drawing process. An additional advantage is that the time spent by the third hand (i.e., the secondary user) for the blood drawing process may now be utilized to attend to other matters.

FIG. 5 illustrates alternating side elevation views of the blood drawing apparatus 501, in a closed state, according to an aspect. As mentioned previously above when referring to FIG. 2, the middle portion 516 of the BDA attachment 515 may comprise inner frames 504, as shown in FIG. 5. As shown, the syringe flanges 503 of the syringe 510 may be encircled by the inner frames 504, such that as the syringe 510 is traversed forward by an exertion of compression forces on the BDA and syringe flanges 519 and 503, respectively, the syringe flanges 503 are caused to slide along the length of and within inner frames 504, as an example, during the blood drawing process. As such, the syringe barrel (e.g., 413 in FIG. 4) is traversed forward smoothly and in a controlled fashion, such that to reduce any movement or adjusting of the needle attached to the syringe hub 518, which would cause unwanted pain to the patient during blood drawing. Thus, an advantage is that pain incurred from the unintentional moving of a needle in a patient's vein may be avoided.

Figure 6A:
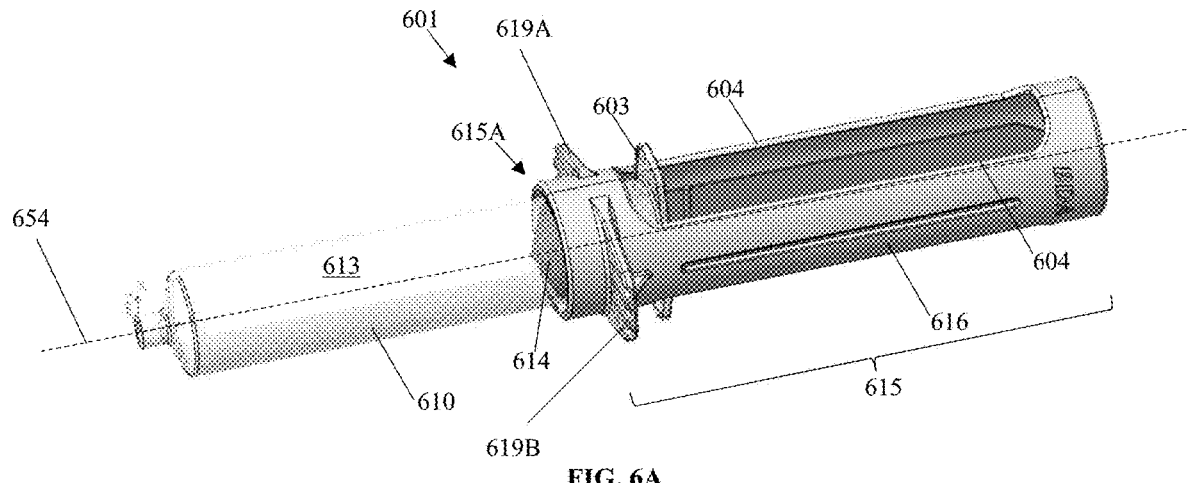
FIGS. 6A-6C illustrate a side and front perspective views, and a perspective cross-sectional view, respectively, of the blood drawing apparatus, in an open state, according to an aspect.
Figure 6B:
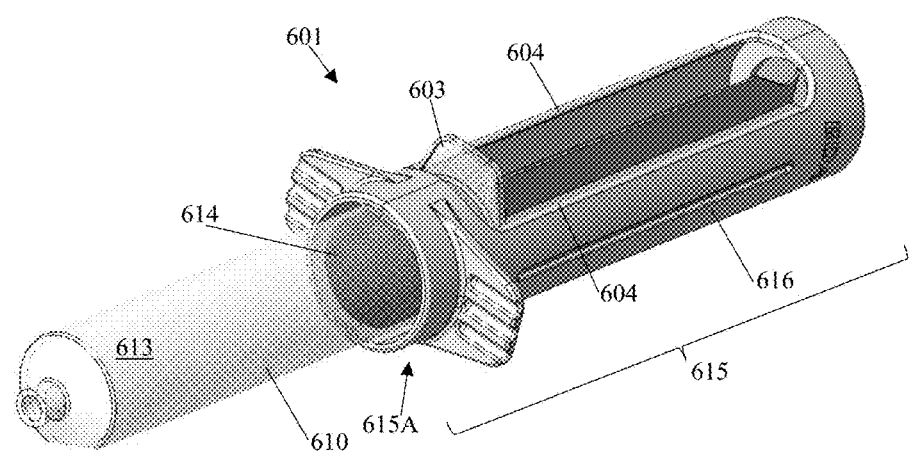
Figure 6C:
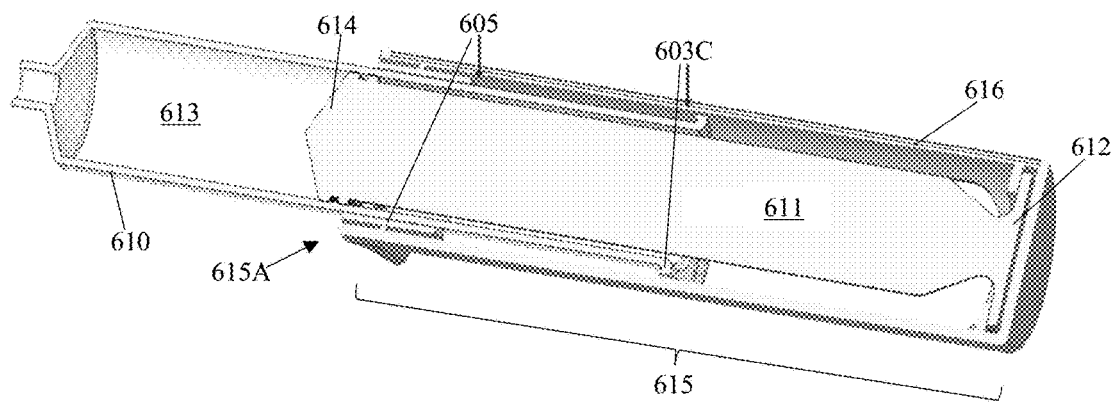

FIGS. 6A-6C illustrate a side and front perspective views, and a perspective cross-sectional view, respectively, of the blood drawing apparatus, in an open state, according to an aspect. As shown in FIGS. 6A-6C, when the blood drawing apparatus 601 is in an open state, the syringe 610 may be fully (fully as possible, for example) extended, such that to protrude forwardly from the first end 615A of the BDA attachment 615, as an example. As described previously above when referring to FIG. 5, the flanges 503 of the syringe may be slid along the inner frames 604 of the BDA medial body 616, for example, such that the forward traversal of the barrel 613 is smooth and controlled. As such, as an example, the syringe 610 may be slidably secured within the BDA attachment 615 while fully extended, as shown in FIGS. 6A-6B. As will be discussed in detail below, the BDA 615 may comprise internal stops to prevent the syringe from overextending and potentially detaching from the plunger seal 614.

As shown by the cross-sectional view in FIG. 6C, the BDA 615 may comprise internal stops 605 attached internally along the medial body 616 and disposed near the first end 615A, as an example. As mentioned previously above, the barrel 613 of the syringe 610 may be offset from a portion of the flanges 603 by a 0.70-inch diameter, for example. As shown in FIG. 6C, the offset portion 603C, when the barrel 613 is traversed forward, may contact the internal stops 605, thus preventing the syringe barrel 613 from overextending and potentially detaching from the plunger seal 614. Such an occurrence would cause the blood (or other bodily liquids) to spill out of the syringe barrel, and thus to be lost and/or spoiled. However, because the offset diameter 603C of the syringe 610 are halted by the inner stops 605 running across an interior side of the medial body 616 of the BDA attachment 615, as shown, and because the plunger top 612 is kept secured to the BDA 615, as will be discussed in detail later, the barrel 613 of the syringe 610 may be kept sealed by the plunger seal 614, thus preventing any leaking or spilling from the syringe 610. Thus, an advantage is that unwanted leaking or spilling from the syringe barrel may be prevented, such that the drawn blood or other liquids may be maintained for further use.

As can be seen in FIG. 6A, the adapter 615, the barrel 613 and their corresponding flanges may be aligned on a sliding axis 654. As described in greater detail herein below, the barrel 613 and the syringe flanges 603 are configured to move along this sliding axis 654. In contrast, the adapter 615 and its corresponding adapter flanges 619A, 619B are configured to remain aligned but stationary on said sliding axis 654, thus allowing for the sliding motion of the barrel 613 along said sliding axis 654 through first end 615A of the adapter 615 to draw a fluid into the syringe 610.

Figure 7A:
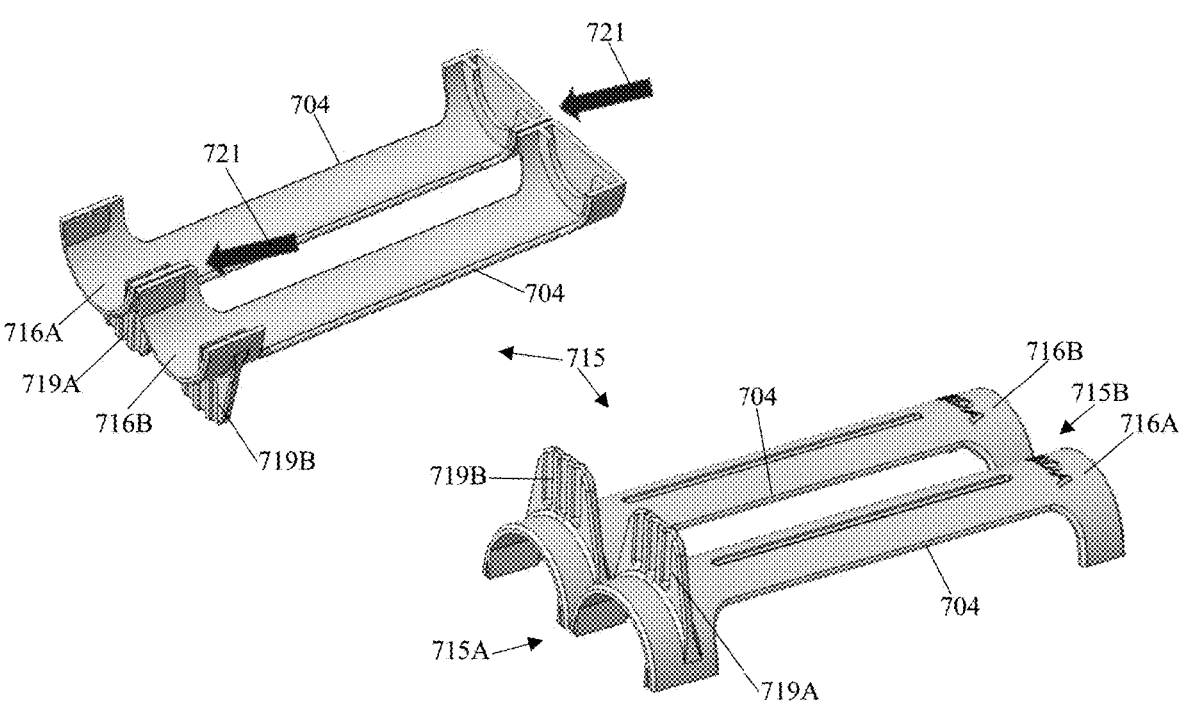
FIGS. 7A-7B illustrate side perspective views, respectively, of an outer attachment of the blood drawing apparatus, in an open and unlocked state, according to an aspect.
Figure 7B:
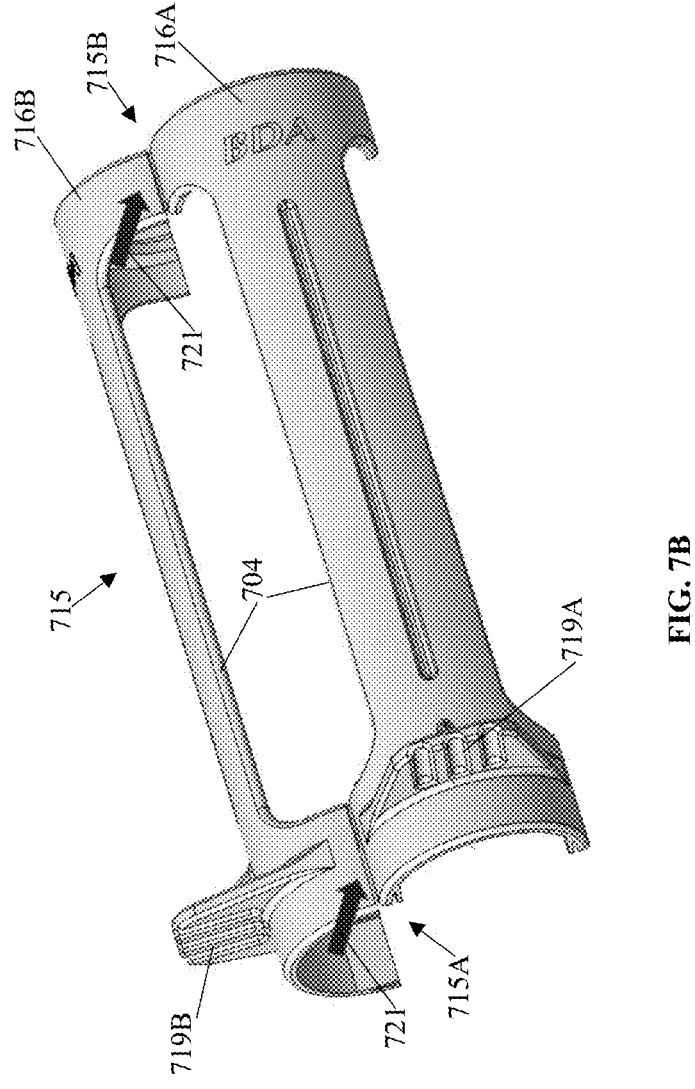

FIGS. 7A-7B illustrate side perspective views, respectively, of an outer attachment 715 of the blood drawing apparatus (not shown), in an open and unlocked state, according to an aspect. As described throughout this disclosure above, the apparatus (not shown) may be provided with a blood drawing assist attachment 715 adapted to surround and secure a syringe, as an example. As will be described herein below, the BDA attachment 715 shown in FIG. 7 may comprise two identical halves 716A and 716B, such that the syringe (not shown) may be removable from the BDA attachment 715, as an example.

As shown in FIGS. 7A-7B, the BDA attachment 715 may be formed by the two identical halves 716A and 716B. As an example, when joined, the two halves 716A and 716B may form the medial portion (e.g., 616 in FIGS. 6A-6B) of the BDA attachment 715. As shown, the two halves 716A and 716B may be attached by a pair of hinges, such as molded hinges 721, for example, each located at one of the first end 715A and at the second end 715B. Additionally, as shown in FIGS. 7A-7B, the molded hinges 721 may be adapted to rotate from 0 to 180 degrees, for example, to allow ease of assembly and disassembly of the BDA attachment 715. As will be discussed in more detail later, the unhinged edges of the two halves 716A and 716B may interlock, when the two halves 716A and 716B abut and form a cylindrical shape, for example, via snap fit components, or other adapter locks described herein, this keeping the BDA attachment 715 slidably secured around the syringe (not shown).

As mentioned above, the two halves 716A and 716B may be identical, such that the two halves 716A and 716B comprise the same exemplary components. As shown in FIGS. 7A-7B, each half 716A, 716B may be provided with na adapter flange 719A, 719B, respectively, a half portion of the inner frames 704, a half portion of each of the first end 715A and the second end 715B, and a snap lock (not shown) for interlocking each half 716A, 716B to the other, as an example. As will be described in detail below, the two halves 716A and 716B may each comprise additional components that interact with the syringe (not shown) for forming the blood drawing apparatus.

Figure 8:
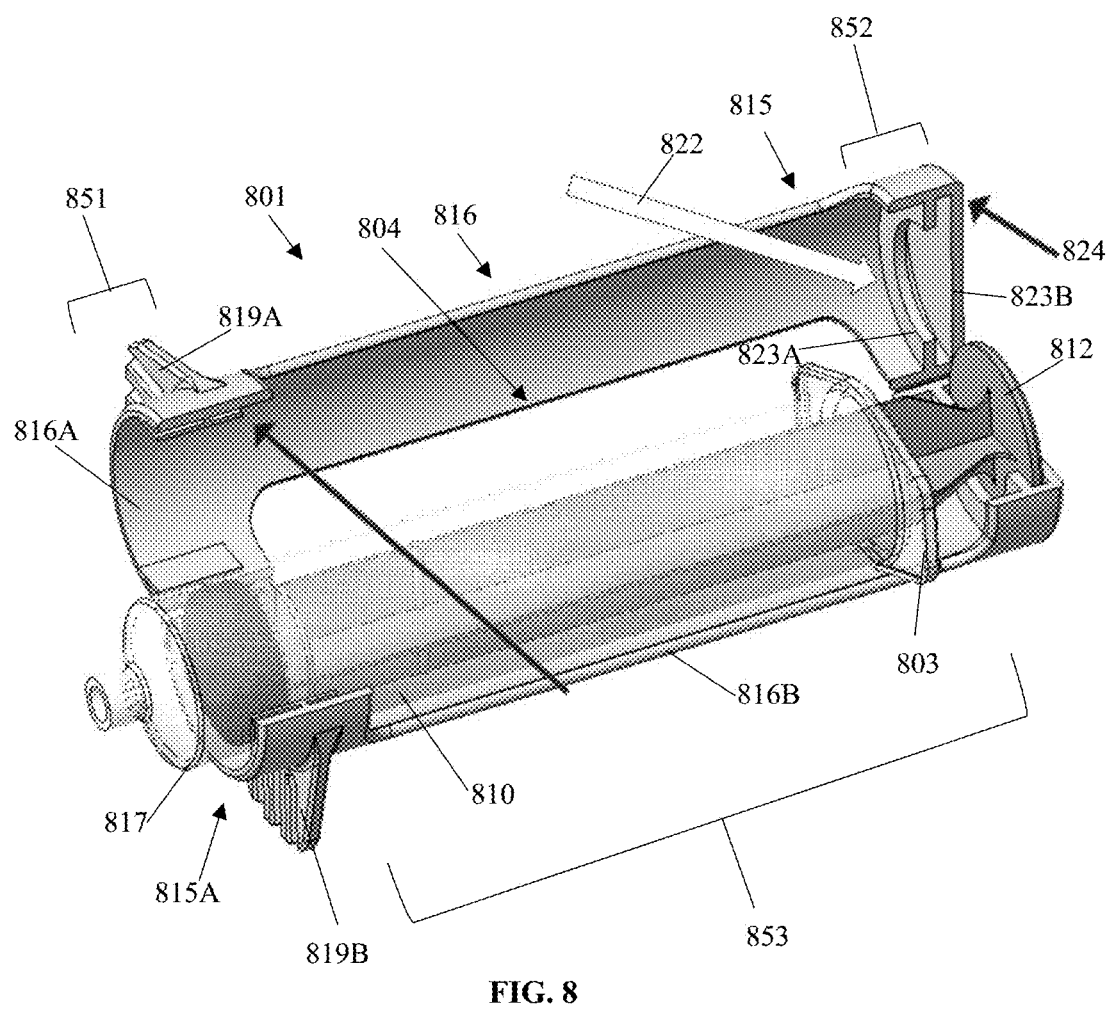
FIG. 8 illustrates a side perspective view of the blood drawing apparatus, with the outer attachment in an open and unlocked state, according to an aspect.

FIG. 8 illustrates a side perspective view of the blood drawing apparatus 801, with the outer attachment 815 in an open and unlocked state, according to an aspect. As mentioned previously above when referring to FIGS. 7A-7B, the BDA attachment may be provided as two identical halves for the easy assembly and disassembly of the blood drawing apparatus. As also mentioned above, each half 816A, 816B of the BDA attachment 815 may comprise the same or substantially the same identical components. Thus, an advantage is that the manufacturing of the BDA attachment may be simplified, which may also reduce manufacturing costs overall.

As shown as an example, when assembling (or disassembling) the apparatus 801, as shown in FIG. 8, the syringe 810 may be positioned within the BDA attachment 815, such that the barrel 813 of the syringe 810 rests atop and abuts the second half 816B of the BDA attachment 815. As shown, at the first end 815A of the BDA attachment 815, the barrel 813 may be encircled by each half 816A, 816B, with the shaft end 817 being slightly protruded out from the first end 815A. At the second end 815B of the BDA attachment 815, as indicated by arrow 822, a press fit configuration is provided for securing and interlocking the plunger top 812 within the BDA attachment 815, as an example. As shown, the press fit configuration 822, divided between each half 816A, 816B, may comprise a first and a second plates/walls 823A and 823B, respectively. As shown, the second plate 823B may form the rear-most surface of the second end 815B and may be adapted to receive and secure a top-most surface of the plunger top 812. Additionally, the first plate 823A may be adapted to receive and secure a bottom-most surface of the plunger top 812 and may comprise an inner diameter ring, as shown, for surrounding and securing the plunger 811 of the syringe 810, for example. Thus, when the first half 816A is rotated and pressed above the syringe 810 and atop the second half 816B, the first and the second plates 823A and 823B may snuggly surround, support and engage with the plunger top 812, such that to prevent the plunger top 812, and thus the plunger 811, from moving during the blood draw process.

As mentioned previously above when referring to FIGS. 7A-7B, each half 816A, 816B of the BDA attachment 815 may be provided with a snap lock, as indicated by arrows 824, for securing the halves 816A and 816B together. As an example, when assembling the apparatus 801, the first half 816A may be rotated and placed atop the second half 816B, and subsequently pressed downwardly with sufficient force, such that to cause an interlocking of the first and the second halves 816A and 816B via the snap locks 824. It should be understood that the orientation of the first and the second halves 816A and 816B may be reversed, for example, such that the first half 816A rests below the second half 816B. As mentioned above, the configuration of the BDA attachment 815 allows for the simple and easy assembly and disassembly of the apparatus 801. As an example, after the blood drawing process is completed, the barrel 813 may be filled (to a predetermined amount, for example), requiring that the syringe 810 be removed and/or replaced. Because of the snap and press locking mechanisms of the halves 816A and 816B, as described above, the BDA attachment 815 may be easily and quickly opened, as shown, allowing the user to remove the used syringe and subsequently collect more blood (or other liquids), as needed, by placing a new syringe into the BDA attachment 815. Thus, an advantage is the ease and simplicity of the assembly and disassembly of the disclosed apparatus, allowing for quick and efficient replacement of apparatus components.

It should be understood that various elements of the disclosed adapter 815 may be simplified into three major components. A guiding collar 851 may be comprised of the structures adjacent to the first end 815A of the adapter, including front portions of the two halves 816A, 816B of the medial body 816, that slidably surrounds and guide the barrel 813 of the syringe 810 as it withdraws fluid, thus preventing movement of the barrel 813 in undesirable directions that may cause pain or discomfort to an individual attached to the blood drawing apparatus 801.

A plunger top restrictor 852 may be comprised of the first and second plates 823A, 823B (e.g., the press fit configuration 822) disposed on the second end 815B of the adapter 815, that are configured to secure the plunger 811 by the plunger top 812 to prevent plunger movement (in relation to the adapter). Alternatively, the plunger top restrictor 852 may omit the second plate 823B, as only the first plate 823A may be required to ensure the plunger 811 remains locked into position during syringe usage and does not travel forward with the barrel 813 during draws.

Finally, a body housing 853 may be disposed between and associated with the guiding collar 851 and plunger top restrictor 852 portions of the adapter 815. This body housing 853 may be comprised of the medial body 816 of the adapter and be configured to keep the guiding collar 851 and the plunger top restrictor 852 a fixed distance apart and suitably aligned to allow smooth, uniaxial movement of barrel 813 during drawing. In the adapter 801 embodiment of FIG. 8, and comparable embodiments described herein, the body housing 853 may include the inner frames 804 configured to both allow the user to visually inspect the fluid entering barrel 813 and suitably limit the potential motion paths of the syringe flanges 803, and thus the barrel 813, to further ensure smooth, axial movement of barrel 813 during drawing, while also preventing the plunger 811 from leaving the barrel 813, to ensure any collected fluid does not leak (e.g., the plunger seal is maintained). Additionally, the adapter 815 may include the adapter flanges 819A, 819B associated with the guiding collar 851 as a "front grip" element to provide a suitable position for a user to manipulate the adapter 801 in conjunction with the syringe flanges 803 to allow for fluids to be drawn into the syringe 810. The guiding collar 851, plunger top restrictor 852 and the body housing 853 of the disclosed adapter 815, as well as a front grip, or their functional equivalents, may be present in each embodiment of the disclosed adapters disclosed herein, as will be described in greater detail hereinbelow.

Figure 9:
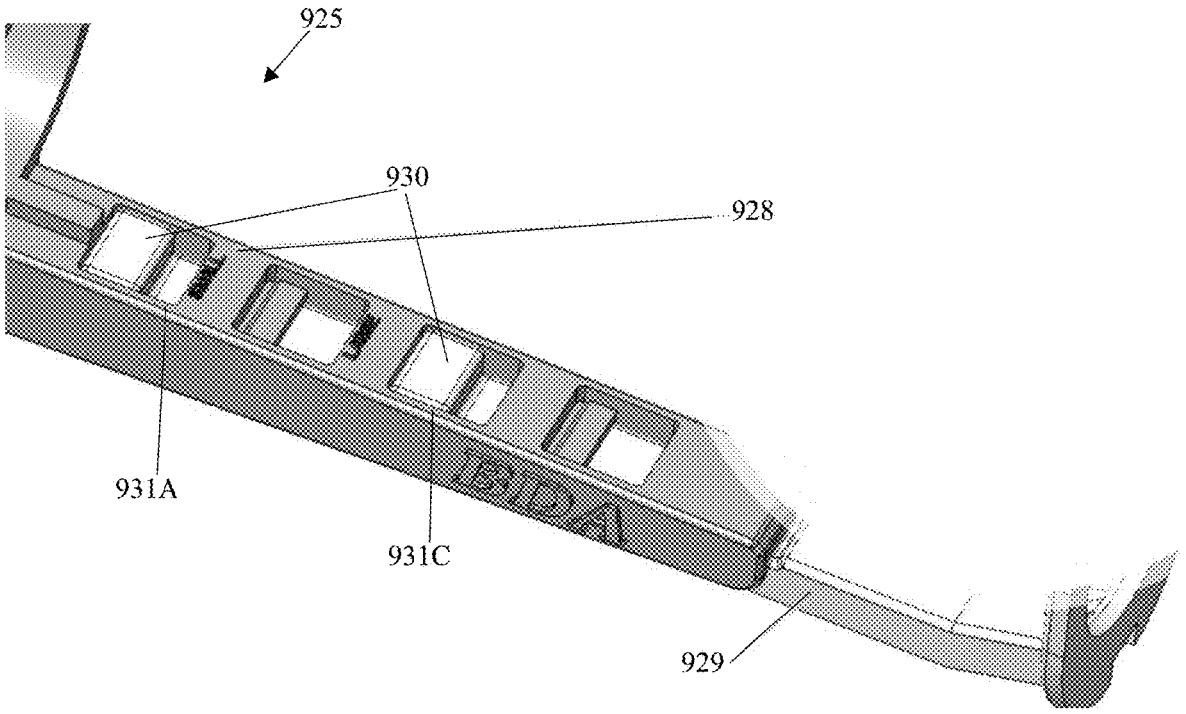
FIG. 9 illustrates a top perspective view of an alternative embodiment of the outer attachment, provided as a telescoping activation arm, according to an aspect.

FIG. 9 illustrates a top perspective view of an alternative embodiment of the outer attachment 915, provided as a telescoping activation arm 925, according to an aspect. As described throughout this disclosure above, the blood drawing apparatus may comprise an outer attachment and a syringe that, together, allow the efficient and effective drawing of blood using only a single hand. As will be described in detail below, the BDA attachment shown previously herein may be provided in an alternative embodiment as the telescoping activation arm 925, which may also enable the drawing of blood without a third hand, as an example.

As shown as an example, the telescoping activation arm ("telescoping activation arm," "blood drawing assist activation arm," "BDA activation arm") 925 may comprise a brace 928 and a telescoping arm 929 slidably connected to the brace 928. As an example, the telescoping arm 929 may be configured to selectively extend/slide (like a telescope, for example), such that to modify (increase/decrease) a length of the telescoping activation arm 925, and thus to accommodate syringes of differing lengths, as will be discussed in more detail later. As shown, the brace 928 of the BDA activation arm 925 may comprise a plurality of slots disposed along, nested within or otherwise associated with a top surface of the brace 928, as an example. Additionally, as shown, the telescoping arm 929 may comprise a plurality of associated notches 930, for example, adapted to slidably engage and interlock within each of the plurality of slots of the brace 928. As an example, a first slot 931A may be disposed near a top end of the brace 928, and, in the example shown in FIG. 9, may be slidably engaged with a notch 930, as shown. Similarly, a third slot 931C, disposed near a center of the brace 928, may be slidably engaged with another notch 930. In this example, because the notches 930 are engaged with the first and the third slots 931A and 931C, respectively, the BDA activation arm 925 may thus be positioned in a first setting ("first setting," "small setting"), as indicated. As will be described in more detail herein later, the small setting of the BDA activation arm 925 may accommodate and support a smaller (i.e., shorter) syringe for use during the blood drawing process, as an example.

Figure 10:
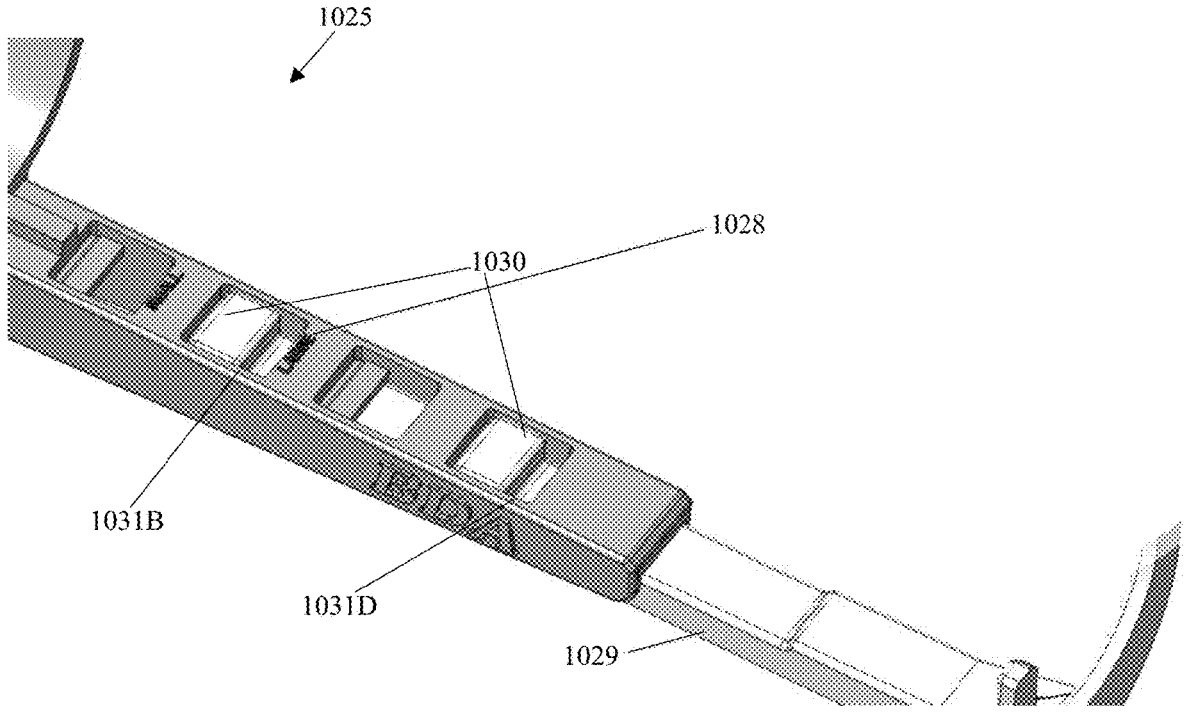
FIG. 10 illustrates a top perspective view of the telescoping activation arm of FIG. 9, in an expanded state, according to an aspect.

FIG. 10 illustrates a top perspective view of the telescoping activation arm 1025 of FIG. 9, in an expanded state, according to an aspect. As mentioned previously above when referring to FIG. 9, the telescoping activation arm 1025 may replace the BDA attachment (e.g., 815 in FIG. 8) described hereinabove. As also described above, the BDA activation arm 1025 may comprise the brace 1028 and the telescoping arm 1029 adapted to slide and thus selectively extend along the brace 1028, as an example.

As similarly described above, the telescoping activation arm 1025 may be provided with a plurality of slots disposed along or nested within the top surface of the brace 1028. Each slot may be adapted to engage with a notch of the plurality of notches 1030 of the telescoping arm 1029, as an example. As shown as an example, a second slot 1031B of the brace 1028 may be engaged with the notch 1030 of the telescoping arm 1029, and a fourth slot 1031D may be engaged with another notch 1030, as shown, such that the BDA activation arm 1025 is extended, for example. In this example, because the notches 1030 are engaged with the second and the fourth slots 1031B and 1031D, respectively, the BDA activation arm 1025 may thus be positioned in a second setting ("second setting," "large setting"), as indicated. As will be described in more detail herein later, the large setting of the BDA activation arm 1025 may accommodate and support a larger (i.e., longer) syringe for use during the blood drawing process, as an example.

Figure 11:
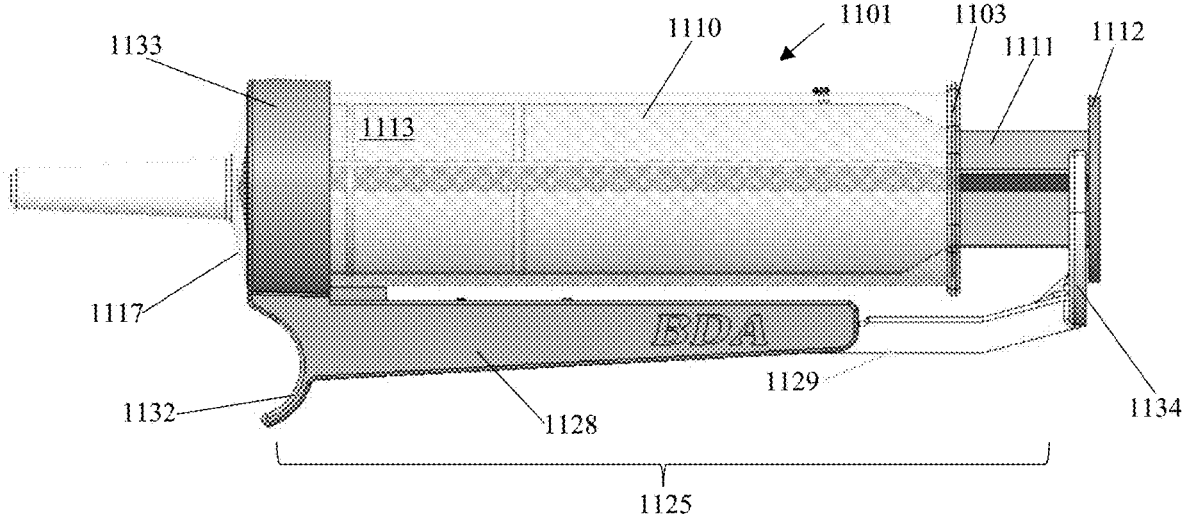
FIG. 11 illustrates a side elevation view of a blood drawing apparatus having the telescoping activation arm of FIG. 9, paired with a small syringe, according to an aspect.

FIG. 11 illustrates a side elevation view of a blood drawing apparatus 1101 having the telescoping activation arm 925 of FIG. 9, paired with a small syringe 1110, according to an aspect. As described previously in this disclosure above, the telescoping activation arm 1125 may be slidably extended, for example, in a small setting or in a large setting, such that to accommodate syringes of various lengths/sizes, as an example. In the example shown in FIG. 11, let the BDA activation arm 1125 be provided in the small setting, as shown previously in FIG. 9, for example, such that a small/short syringe 1110 (e.g., a 50 ML syringe) is provided in the BDA activation arm 1125, as will be described in detail below.

As shown in FIG. 11, the syringe 1110, when the apparatus 1101 is assembled, for example, may rest within the BDA activation arm 1125, such that the barrel 1113 of the syringe 1110 abuts at least a portion of the brace 1128 of the BDA activation arm 1125. As shown, the BDA activation arm 1125 may further comprise a front collar 1133 connected above the brace 1128 and adapted to slidably surround and grip the barrel 1113 near the shaft end 1117 of the syringe 1110, as an example. Additionally, as shown, the BDA activation arm 1125 may comprise a circular grip 1132, disposed along a front edge of the brace 1128, for receiving a finger of a user, as will be described in more detail later. Finally, as shown, the BDA activation arm 1125 may further comprise a rear U-ring ("U-ring") 1134 attached at an end of the telescoping arm 1129, as an example. Like the press fit configuration (e.g., 822) of the BDA attachment shown previously in FIG. 8, the U-ring 1134 may be configured to surround the plunger 1111 and securely hold the plunger top 1112, such that to prevent the plunger 1111 from moving or shifting during the blood drawing process.

As similarly described throughout this disclosure above, the BDA activation arm 1125 may secure the syringe 1110, such that the barrel 1113 of the small syringe 1110 is caused to move (by the exertion of an outside force) rather than the plunger 1111, as in traditional blood drawing methods. As such, to draw blood (or other liquids) into the barrel 1113 of the syringe 1110, the user, after the needle (not shown) has been inserted into a vein (or other body part) of the patient, may grip the apparatus 1101 by placing an index or middle finger onto the circular grip 1132, and by placing a thumb (of the same hand) onto the syringe flange 1103, as an example. Then, the user may exert a frontal force onto the circular grip 1132 (via the index or middle finger) while simultaneously exerting a rear force onto the syringe flange 1103 (via the thumb), such that to cause the barrel 1113 to traverse forwardly through the front collar 1133, thus filling the barrel 1113 with blood (or other liquids). In this way, the barrel 1113 may be filled with blood, as desired, while the plunger 1111 is kept stationary within the U-ring 1134, thus preventing any unwanted movement at the needle entry point. As mentioned previously throughout this disclosure above, the exertion of the rear pushing force (by the thumb) may be easier for the user, than a pulling of the plunger top 1112, as in traditional syringes, such that a third hand is not needed for the drawing of blood into the small syringe 1110.

It should be understood that the described pushing forces described in FIG. 11 are roughly comparable to the forces described in FIG. 8.

Figure 12:
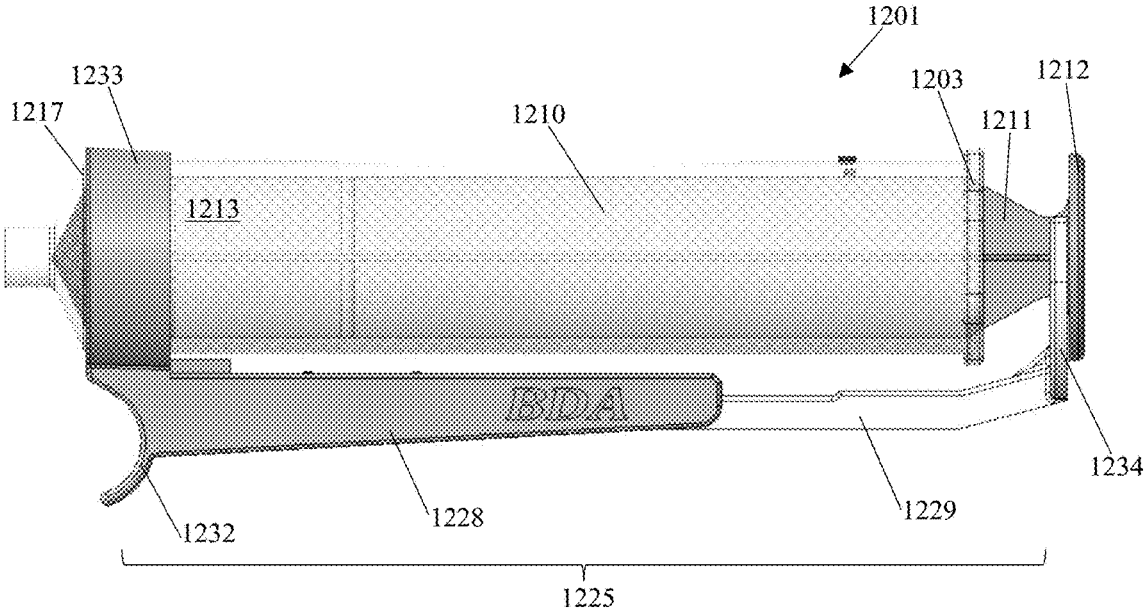
FIG. 12 illustrates a side elevation view of the blood drawing apparatus having the telescoping arm of FIG. 10, paired with a large syringe, according to an aspect.

FIG. 12 illustrates a side elevation view of the blood drawing apparatus 1201 having the telescoping arm 1025 of FIG. 10, paired with a large syringe 1210, according to an aspect. As described previously in this disclosure above, the telescoping activation arm 1225 may be slidably extended, for example, in a small setting or in a large setting, such that to accommodate syringes of various lengths/sizes, as an example. In the example shown in FIG. 12, let the BDA activation arm 1225 be provided in the large setting, as shown previously in FIG. 10, for example, such that a large/long syringe 1210 (e.g., a 60 ML syringe) is provided in the BDA activation arm 1225, as will be described in detail below.

As shown in FIG. 12, the syringe 1210, when the apparatus 1201 is assembled, for example, may rest within the BDA activation arm 1225, such that the barrel 1213 of the syringe 1210 abuts at least a portion of the brace 1228 of the BDA activation arm 1225. As shown, the BDA activation arm 1225 may further comprise the front collar 1233, as similarly described above, connected above the brace 1228 and adapted to surround and grip the barrel 1213 near the shaft end 1217 of the syringe 1210, as an example. Additionally, as shown, the BDA activation arm 1225 may comprise the circular grip 1232, disposed along the front edge of the brace 1228, for receiving a finger of a user, as described previously above. Finally, as shown, the BDA activation arm 1225 may further comprise the rear U-ring 1234 attached at the end of the telescoping arm 1229, as an example. As described previously when referring to FIG. 11 above, the U-ring 1234 may be configured to surround the plunger 1211 and to securely hold the plunger top 1212, for example, such that to prevent the plunger 1211 from moving or shifting during the blood drawing process.

As similarly described above when referring to FIG. 11, the BDA activation arm 1225 may secure the syringe 1210, such that the barrel 1213 of the large syringe 1210 is caused to move (by the exertion of an outside force) rather than the plunger 1211, as in traditional blood drawing methods. As such, to draw blood (or other liquids) into the barrel 1213 of the syringe 1210, the user, after the needle (not shown) has been inserted into a vein (or other body part) of the patient, may grip the apparatus 1201 by placing an index or middle finger onto the circular grip 1232, and by placing a thumb (of the same hand) onto the syringe flange 1203, as an example. Then, the user may exert a frontal force onto the circular grip 1232 (via the index or middle finger) while simultaneously exerting a rear force onto the syringe flange 1203 (via the thumb), such that to cause the barrel 1213 to traverse forwardly through the front collar 1233, thus filling the barrel 1213 with blood (or other liquids). In this way, the compression of the circular grip 1232 and the syringe flange 1203 may cause the barrel 1213 to be filled with blood, as desired, while the plunger 1211 is kept stationary within the U-ring 1234, thus preventing any unwanted movement at the needle entry point. As mentioned previously throughout this disclosure above, the exertion of the rear pushing force (by the thumb) may be easier for the user, than a pulling of the plunger top 1212, as in traditional syringes, such that a third hand is not needed for the drawing of blood into the large syringe 1210.

It should be understood that the particular diameters of the collar 1233 and of the U-ring 1234 may be varied, during manufacturing, for example, such that to accommodate syringe barrels and/or plungers that may be wider or narrower than those of traditional syringes, as an example. Thus, an advantage of the above-described apparatus is the ability to accommodate syringes of varying lengths and/or size. Another advantage is that, during the blood drawing process for larger syringes, the need for assistance from a third hand may be negated.

Figure 13:
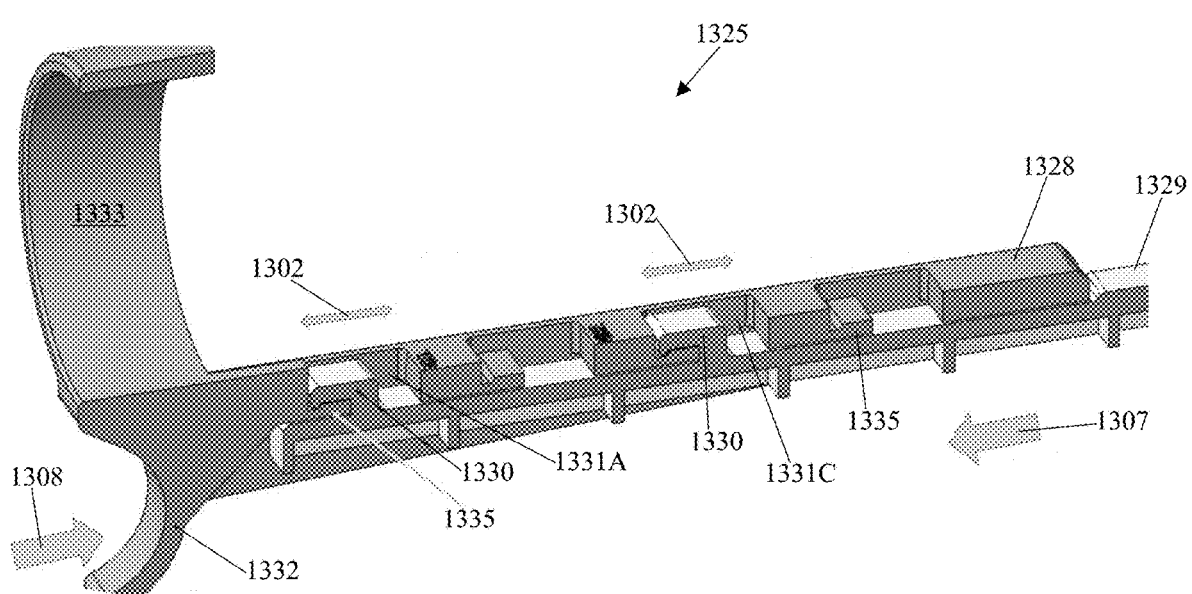
FIG. 13 is a diagram illustrating a perspective sectional view of the telescoping activation arm, according to an aspect.

FIG. 13 is a diagram illustrating a perspective sectional view of the telescoping activation arm 1325, according to an aspect. As mentioned previously in this disclosure above, the telescoping activation arm 1325 may be adapted to be extendable, such that to accommodate syringes of various lengths, for example. As will be described in detail below, the telescoping activation arm 1325 may employ a slide and lock technique that not only adjusts the length of the telescoping activation arm 1325, but also prevents adjustment of the telescoping arm 1325 during the blood drawing process.

As shown in FIG. 13, the telescoping activation arm 1325 may comprise the brace 1328 slidably engaged with the telescoping arm 1329, as an example. As described previously in this disclosure above, the brace 1328 may be provided with a plurality of slots disposed along a top surface of the brace 1328, and the telescoping arm 1329 may be provided with a plurality of notches 1330 adapted to be slid into each of the plurality of slots, as an example. As shown, each slot of the plurality of slots may be provided with a snap lock 1335, for example, adapted to engage with a notch of the plurality of notches 1330. As an example, when adjusting the length of the telescoping activation arm 1325, a first notch 1330 may be inserted into the first slot 1331A, while a second notch 1330 is inserted into the third slot 1331C, for example. Once the notches 1330 are inserted through the first and the third slots 1331A and 1331C, the telescoping arm 1329 may be pushed forward, as indicated by 1302, such that to cause the notches 1330 to engage with the snap locks 1335, as shown in FIG. 13. The same process may be employed when locking the notches 1330 within the other slots of the brace 1328. It should be understood that a user may perform the adjustment of the telescoping arm length prior to drawing blood, and that the process may be observed and monitored from above (i.e., user looking straight down over the top of the brace 1328).

As outlined above, the length of the BDA activation arm 1325 may be easily and effectively adjusted, as needed, for accommodating various sizes of syringes. Thus, an advantage is the ease of adjustability and thus the user-friendly nature of the disclosed telescoping activation arm. As an example, during use of the apparatus (e.g., 1201 in FIG. 12), as described previously above, the user may apply a compression force onto the apparatus via the circular recess 1332 of the BDA activation arm 1325 and the syringe flange (e.g., 1203). As shown, as the user exerts the frontal exertion force, indicated by 1308, the plunger (e.g., 1211 in FIG. 12) may exert an equal and opposite reaction force, indicated by 1307, as an example. Because the reaction force 1307 is oriented in the same direction as the locking exertion force 1302, for example, the telescoping arm 1329 and the brace 1328 are kept interlocked, as shown in FIG. 13. Thus, during use of the apparatus (not shown) for drawing blood from a patient, the BDA activation arm 1325 may remain securely locked, such that instances of device failure, syringe leakage, or induction of pain in the patient, are effectively prevented, and avoided, as benefits.

Figure 14:
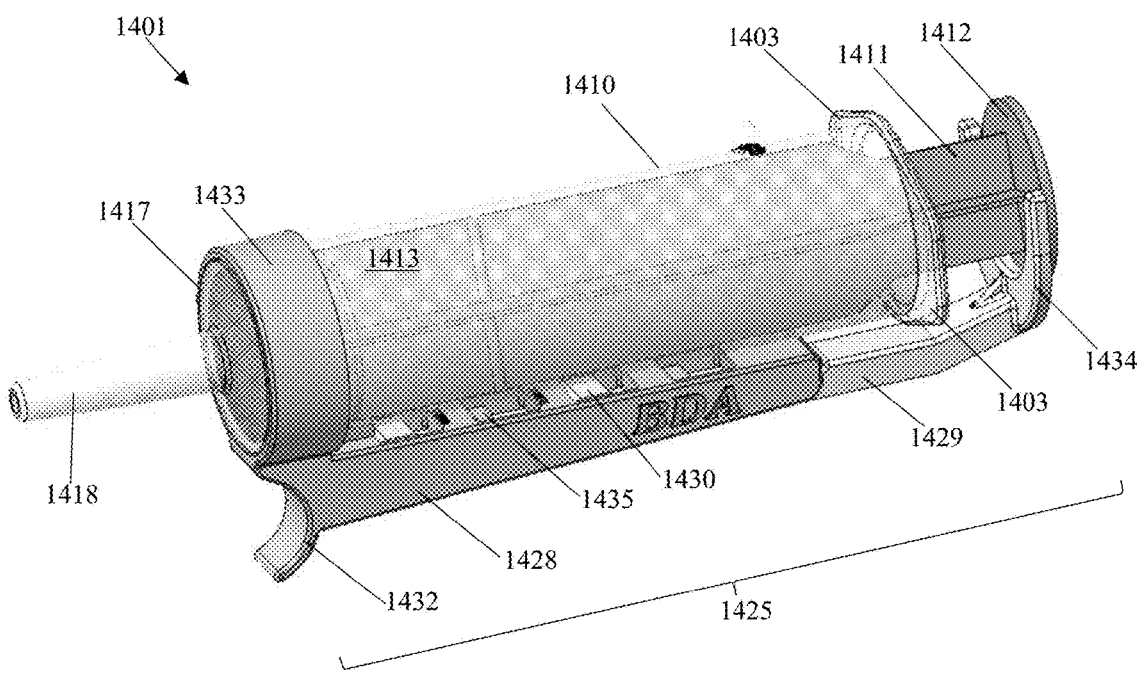
FIG. 14 illustrates a perspective view of the blood drawing apparatus, in a closed state, according to an aspect.

FIG. 14 illustrates a perspective view of the blood drawing apparatus 1401, in a closed state, according to an aspect. As described previously herein above, the apparatus 1401 may enable the efficient and effective drawing of blood (or other liquids) from a vein (or other body part) of a patient by a user (e.g., a nurse, care provider, doctor, etc.), without the need for a third hand (e.g., a second nurse, care provider, doctor, etc.). As shown in FIG. 14, the apparatus 1401 may comprise the syringe 1410 secured within the BDA activation arm 1425. As similarly described above, the user may apply a compression force (via index/middle finger and thumb, for example) onto the circular recess 1432 and the syringe flange 1403, such that to cause the barrel 1413 of the syringe 1410 to be traversed in a forward direction through the collar 1433 of the BDA brace 1428. As the barrel 1413 is driven forwardly, a vacuum, like in traditional syringes, is expanded, such that to draw blood (or other fluids) into the barrel 1413 via the hub 1418, as an example.

Simultaneously, the collar 1433 keeps the barrel 1413 secured and horizontal, for example, such that to prevent unintentional jolts or shifts of the needle inserted into the patient's vein, which would cause pain to the patient. Moreover, the U-ring 1434 connected to the telescoping arm 1429 may secure and hold the plunger top 1412, as shown in FIG. 14, such that to prevent the plunger 1411 from moving during use, which could lead to leakage of the barrel 1413, for example. Finally, when the barrel 1413 is fully extended, and thus full of blood (or other liquids), the syringe flange 1403 is stopped by an interior edge of the collar 1433, such that to prevent the barrel 1413 from completely detaching from the plunger 1411. In this way, leakage and/or spilling of the barrel contents is prevented. Once the blood drawing process has been completed, as an example, the syringe 1410 may be removed from the BDA activation arm 1425 by lifting the plunger top 1412 upwardly, such that to disengage from the U-ring 1434, and subsequently carefully pulling the syringe backwardly, such that to remove the barrel 1413 from the collar 1433. Thus, the syringe 1410 may be easily and quickly removed, as described, allowing the user to subsequently collect more blood (or other liquids), as needed, by placing a new syringe into the BDA activation arm 1425. Thus, an advantage is the ease and simplicity of the assembly and disassembly of the disclosed apparatus, allowing for quick and efficient replacement of apparatus components.

Figure 15:
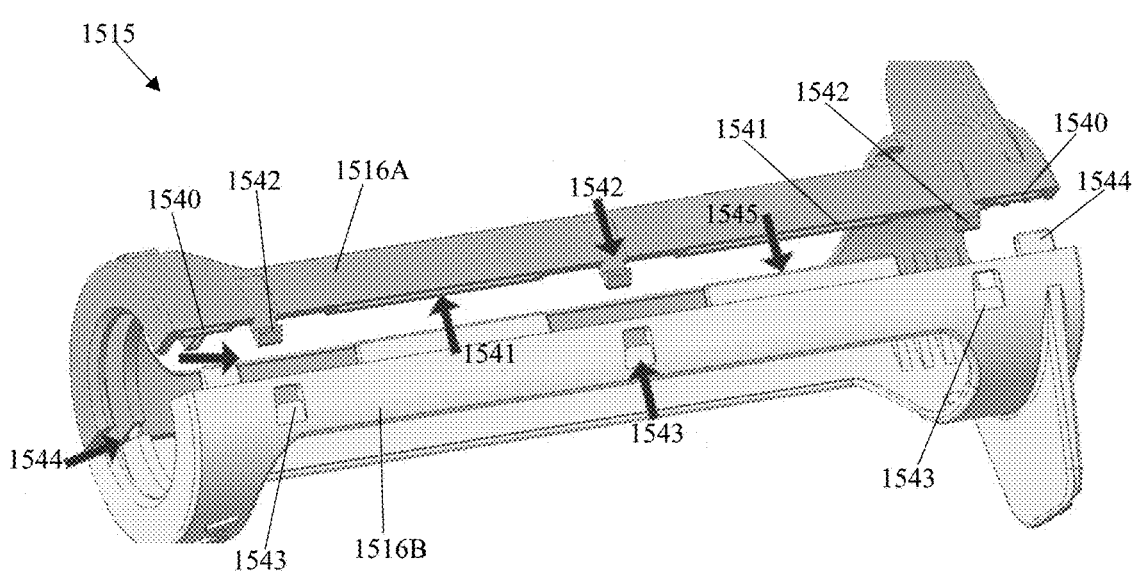
FIG. 15 illustrates a side perspective view of the outer attachment of FIGS. 7A-7B, showcasing an exemplary locking mechanism of the outer attachment, according to an aspect.

FIG. 15 illustrates a side perspective view of the outer attachment 715 of FIGS. 7A-7B, showcasing an exemplary locking mechanism of the outer attachment 1515, according to an aspect. As described previously above when referring to FIGS. 7A-7B, the medial body of the BDA 715 may comprise a first and a second identical halves 716A and 716B joined by molded hinges, for example. As will be described in detail below, the halves may be provided with a tab and hook-based locking mechanism, for example, such that to allow the unhinged portions of the halves to be securely interlocked, as an example.

As shown in FIG. 15, the first half 1516A of the BDA 1515/medial body may comprise a plurality of first slots 1540, a plurality of second slots 1541, and a plurality of snap hooks 1542. The second half 1516B, as an example, may comprise a plurality of locking slots 1543, a plurality of first tabs 1544, and a plurality of second tabs 1545, as shown. As indicated, upon engagement of the first half 1516A with the second half 1516B, the plurality of first tabs 1544 may each be inserted into each of the plurality of first slots 1540, the plurality of second tabs 1545 may each be inserted into each of the plurality of second slots 1541, and the plurality of snap hooks 1542 may each be inserted into each of the plurality of locking slots 1543, respectively. As will be discussed in more detail below, the engagement of the first half 1516A with the second half 1546B via the exemplary tab and hook-based locking mechanism outlined above may enable a syringe to be slidably supported within the BDA 1515 upon assembly, as an example.

Figure 16A:
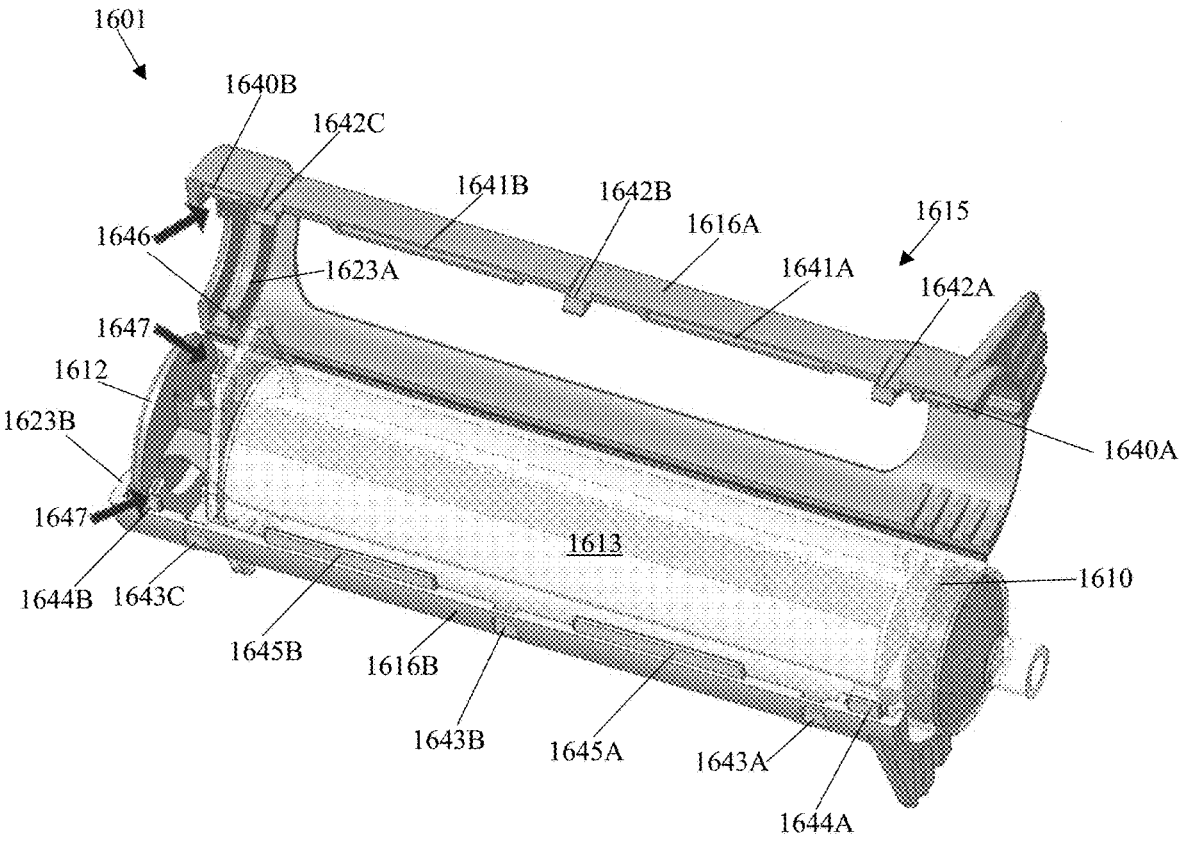
FIGS. 16A-16B illustrate side perspective views of the blood drawing apparatus, with the outer attachment in an open and unlocked state and in a closed state, respectively, according to an aspect.
Figure 16B:
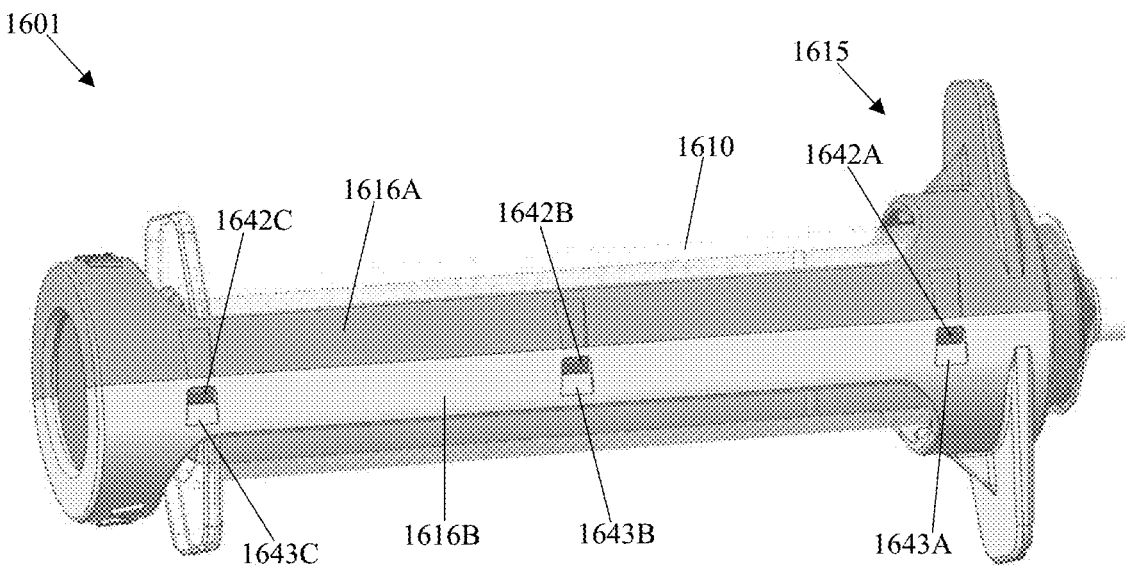

FIGS. 16A-6B illustrate side perspective views of the blood drawing apparatus 1601, with the outer attachment 1615 in an open and unlocked state and in a closed state, respectively, according to an aspect. As similarly described previously above when referring to FIG. 8, the two halves (e.g., 816A and 816B) of the BDA (e.g., 815) disclosed herein may enable the easy assembly and disassembly of the blood drawing apparatus. Furthermore, as will be described in detail below, the interlocking of the two halves may keep the syringe secured within the BDA, such that blood or other bodily fluids may be effectively drawn into the barrel of the syringe, as an example.

As shown in FIG. 16A, the syringe 1610 may be placed atop and within the second half 1616B of the BDA 1615 for assembling of the apparatus 1601, for example. As discussed previously above when referring to FIG. 8, each half 1616A, 1616B may comprise a portion of a first and a second plates/walls 1623A and 1623B, (e.g., the press fit configuration 822 of FIG. 8), as shown. As shown in FIG. 16A, the portion of the first wall 1623 on the first half 1616A may comprise holding slots 1646, and the portion of the first wall 1623 on the second half 1616B may comprise corresponding holding tabs 1647, as an example. As described previously in this disclosure above, the first and the second walls 1623A and 1623B may snugly abut and secure the plunger top 1612 of the syringe 1610, as an example. The holding slots 1646 and the holding tabs 1647, when inserted and engaged with each other, for example, may secure each half of the first and the second walls 1623A and 1623B together, such that to prevent deflection from a reaction force from the plunger (e.g., 1411 in FIG. 14), during a drawing of blood, for example. Thus, the plunger top 1612 may be secured and prevented from moving during the blood drawing process.

As described previously above when referring to FIG. 15, the first and the second halves 1616A and 1616B may be provided with a hook and tab-based locking mechanism for securing halves together, as an example. As shown in FIG. 16A, and continuing the example above, when assembling the apparatus 1601, the first half 1616A may be rotated over and atop the barrel 1613 of the syringe 1610 from the top, for example. As the first and the second halves 1616A and 1616B are brought together, the pluralities of first and second tabs may enter the pluralities of first and second slots, respectively. As such, for example, the tab 1644A may be inserted into the slot 1640A and the tab 1644B may be inserted into the slot 1640B, respectively. Additionally, for example, the tabs 1645A and 1645B may be inserted into the slots 1641A and 1641B, respectively, as shown. The insertion of each of the pluralities of first and second tabs into each of the pluralities of first and second slots, respectively, may guide the subsequent alignment of the snap hooks and the locking slot, for example, as well as prevent the first and the second halves 1616A and 1616B from deflecting outwardly from the snap hooks.

Continuing the above example, as the first and the second halves 1616A and 1616B are further engaged (via the pluralities of tabs and slots, as mentioned above), the plurality of snap hooks may be fully inserted into and interlocked within the plurality of locking slots, respectively. As such, for example, each of the snap hooks 1642A, 1642B, and 1642C may slide into, and subsequently be hooked to, each of the locking slots 1643A, 1643B, and 1643C, respectively. As such, the first half 1616A may be securely interlocked with the second half 1616B, such that the syringe 1610 may be encased by the BDA 1615, as shown in FIG. 6B, allowing smooth and controlled movement of the syringe 1610 for drawing of blood and other bodily fluids, for example. It should be understood that the number of slots, hooks, and/or tabs depicted in the drawings and described above is exemplary, and thus that a grater or fewer number of such components may be provided, as needed.

It should be understood that the disclosed apparatus and methods may be employed in other fields other than medicine or animal care, as in, essentially, any field that may require or benefit from an apparatus adapted to draw liquids into a large syringe using only one hand, for example. It should also be understood that the disclosed appearance, shape, and/or dimensions of the disclosed apparatus and its exemplary components may be altered without veering outside of the scope of the current invention. It should also be understood that alternative embodiments of the BDA attachment or BDA activation arm may be provided that are not explicitly shown or described herein, but that in essence function to draw fluids into a syringe by pushing forwards, for example, and thus are still captured in scope by the above description.

Figures 17A, 17B:
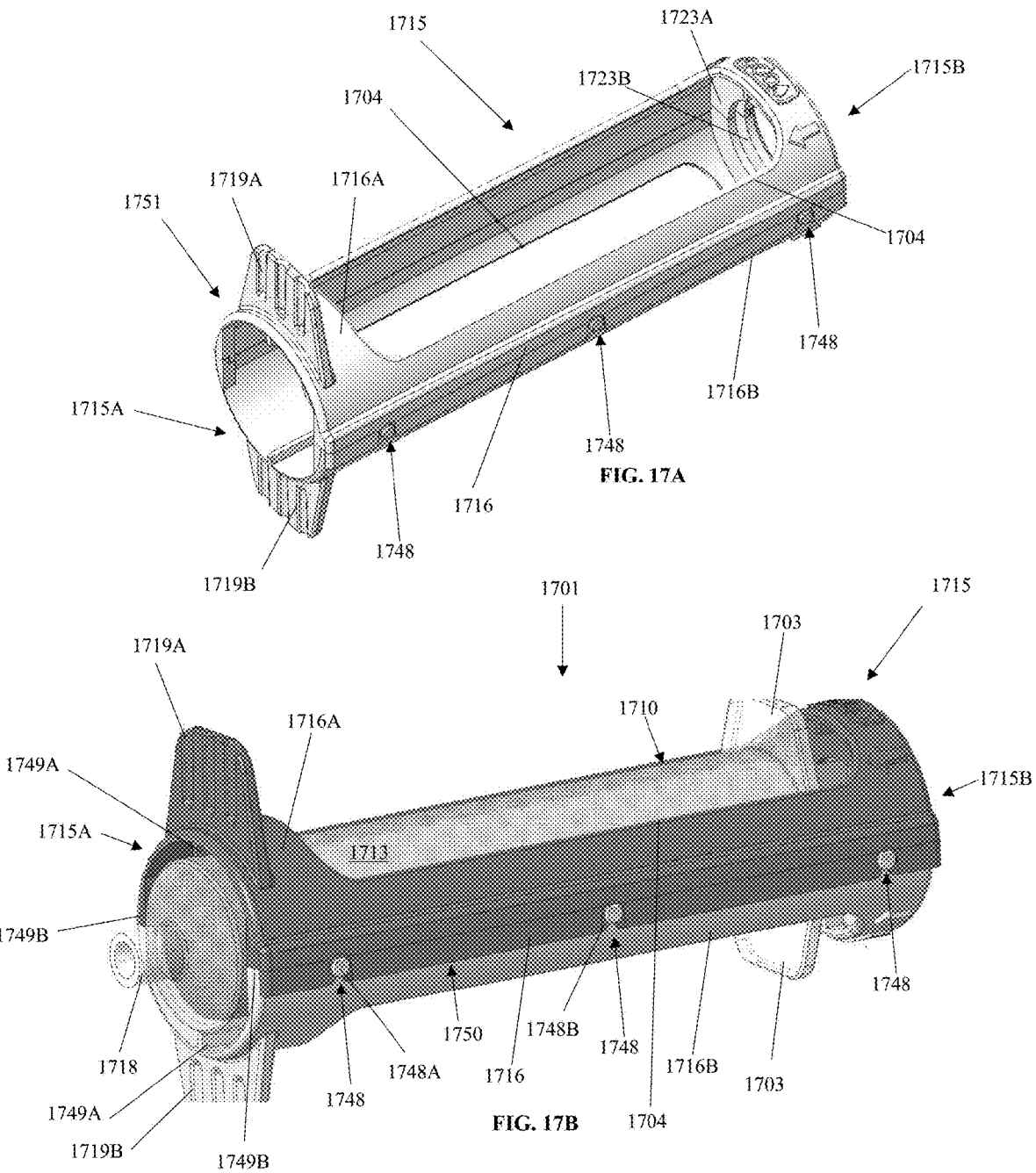
FIG. 17A-17B illustrates perspective views of an outer attachment of a blood drawing apparatus and a blood drawing apparatus, in a closed state, respectively, according to an aspect.

FIG. 17A-17B illustrates perspective views of an outer attachment 1715 of a blood drawing apparatus and a blood drawing apparatus 1701, in a closed state, respectively, according to an aspect. As disclosed hereinabove, a plurality of different locking mechanisms may be implemented in order to further associate the two halves 1716A, 1716B of the adapter 1715 of the blood drawing apparatus 1701, to allow said adapter 1715 surround a syringe 1710, while still allowing the barrel 1713 to slide as needed. One additional exemplary locking mechanism for associating/locking the first and second halves 1716A, 1716B together is a knob lock 1748 disclosed in FIG. 17A-17B. Each knob lock 1748 may be comprised of a securing knob 1748A disposed on the second half 1716B of the medial portion 1716, that is configured to be securely engaged with or be seated within a locking pocket 1748B disposed within the first half 1716A of the medial body 1716A.

The securing knob 1748A and locking pocket 1748B of each knob-lock 1748 may be configured such that upon the adapter 1715 being folded into a closed configuration, as seen in FIG. 17A-17B, each securing knob 1748A is configured to be engaged with or seated within the corresponding locking pocket 1748B to secure the two halves 1716A, 1716B of the medial body 1716 together, thus reversibly securing the blood drawing apparatus 1701 together around a syringe 1710. The knob lock 1748 may also utilize a securing ridge, such as securing ridge 1848C of FIG. 18A, secured to or associated with the second half 1716B that is configured to engage with a securing slot, such as securing slot 1848D of FIG. 18A, nested within the first half 1716A, in order to ensure a secure interconnection/association of the two halves 1716A, 1716B, as will be described in greater detail later.

The adapter 1715 of FIG. 17A-17B may be similar to adapter 715 of FIG. 7A-7B, with one notable exception being the utilization of the herein disclosed knob locks 1748 of FIG. 17A-17B in lieu of the mentioned snap locks (not shown). The knob locks 1748 may have a different structure when compared to the snap locks disclosed previously, as the securing knob 1748A of a knob lock 1748 is outwardly visible, even upon engaging within the corresponding locking pocket 1748B. This structure of the knob lock 1748 may make it easier to engage and disengage the two halves 1716A, 1716B of the medial body 1716. The specific structure of the disclosed knob locks 1748 and their components will be described in greater detail later. As seen in FIG. 17A, an adapter may utilize three equidistantly positioned knob locks 1748 but may also use different quantities/positioning as needed.

As with prior disclosed variations of the adapter, said adapter 1715 may have pair of adapter flanges 1719A, 1719B disposed near a first end 1715A of the adapter 1715. As disclosed above, a user may use a singular hand to apply a compression force between (e.g., simultaneously to) the adapter flanges 1719A, 1719B and the syringe flanges 1703 in order to cause the barrel 1713 of the syringe 1710 to traverse forward through the first end 1715A of the adapter 1715, thus causing blood or another fluid to be drawn into the barrel 1713 via the top hub 1718. The disclosed adapter 1715 may utilize the same mechanisms disclosed hereinabove to secure the plunger top (not shown) of the syringe 1710 in place within the adapter 1715, including the first and second plates, 1723A and 1723B, respectively, configured to confine and secure the plunger top, as described hereinabove, wherein the first and second plates 1723A, 1723B are disposed near the second end 1715B of the adapter 1715. As with previous attachment mechanisms, the components of the knob locks 1748 may be disposed within or associated with the medial body 1716 and disclose herein.

The improved locking mechanism of the knob lock 1748 may provide several advantages over the hereinabove described locking mechanisms, such as the aforementioned snap locks. These advantages may include faster and easier engagement and disengagement of the two halves 1716A, 1716B, as well as a more secure engagement of the two halves 1716A, 1716B. For engagement and disengagement of the two halves 1716A, 1716B, a user may easily manipulate each exposed securing knob 1748A to insert or remove it from its corresponding locking pocket 1748B for rapid addition, removal or replacement of a syringe 1710 to/from the adapter 1715. Additionally, the span of the corresponding first half 1716A of the medial body 1716 disposed between the locking pockets 1748B creates a lip 1750 that a user may manipulate in conjunction with the exposed securing knob(s) 1748A to easily and rapidly pry open the outer attachment 1715 as needed.

As can be seen in FIG. 17A-17B, alignment fins 1749A longitudinally disposed within the first end of the adapter 1715 (e.g., within the guiding collar 1751) are configured to ensure proper positioning of the barrel 1713 of the syringe 1710 as it traverses through the first end 1715A (e.g., the barrel guide) of the adapter 1715 during a blood/fluid drawing. These alignment fins 1749A further ensure smooth, axial movement of the barrel 1713 to prevent the movement of said barrel 1713 from causing unexpected and undesirable movements at a needle entry point that may cause pain or discomfort for an individual from which blood/fluid is being drawn. It should be understood that more than two alignment fins 1749A may be provided, and in different positions within the guiding collar 1751, as long as said alignment fins 1749A suitably allow smooth, axial motion of the barrel 1713 as it travels through the guiding collar 1751

These alignment fins 1749A may work in conjunction with alignment plates 1749B disposed within the guiding collar 1751/first end 1715A of the adapter 1715, to allow the barrel 1713 to traverse forward through the barrel guide smoothly and easily with minimal friction while avoiding undesirable transversal motion (e.g., bending in a direction away from intended axis of motion, the sliding axis). The alignment plates 1749 may be disposed on adjoining ends of the two halves 1716A, 1716B of the medial body 1716. In addition to coordinating with the alignment fins 1749A to ensure that the barrel 1713 may suitably traverse through the guiding collar 1751, the alignment plates 1749B may also increase the structural integrity of the adapter by increasing the thickness of each medial body half 1716A, 1716B at the locations at which they interconnect or adjoin (the hinge and locking mechanism positions). As will be discussed hereinbelow, the guiding collar 1751 may be referred to as a type of barrel guide. These alignment plates 1749B may also operate as the prior described internal stops 605 of FIG. 6 to prevent the barrel 1713 from overextending, thus preventing leakage of the collected fluid.

As can be seen when comparing adapter 1715 of FIGS. 17A-17B to adapter 715 of FIGS. 7A-7B, the positioning of their corresponding inner frames, 1704, 704, respectively may vary. As can be seen in adapter 715 of FIGS. 7A-7B, the inner frames 704 may be formed as a result of the association of the two half frame structures on each body half 716A, 716B, such that each medial body half contains two non-adjoined halves of the opposing inner frames 704. In contrast, each body half 1716A, 1716B of the adapter 715 of FIB 17A-17B may contain a singular inner frame 1704 nested within the half medial body. As a result of the positioning of each adapter flange 719A, 719B/1719A, 1719B on corresponding half 716A, 716B/1716A, 1716B of the medial body, the resultant positioning of the adapter flanges in relation the syringe flanges of a held syringe may vary between the two embodiments. In adapter 715 of FIGS. 7A-7B, the inner frames may be described as being disposed between the two halves 716A, 716B of the adapter 715, whereas in adapter 1715 of FIGS. 17A-17B, each inner frame 1704 may be described as being nested or disposed within a corresponding half 1716A, 1716B of the adapter 1715.

In FIG. 6A, the positioning of each inner frame 604 between the two halves 616A, 616B of the medial body results in the encircled syringe flanges 603 being radially rotated 90 degrees compared to the rotation of the adapter flanges 619A, 619B present on the same sliding axis 654. In contrast, as seen in FIG. 17B, the positioning of each inner frame 1704 within a corresponding half 1716A, 1716B of the medial body 1716 results in the adapter flanges 1719A, 1719B and the syringe flanges 1703 being radially aligned (0 degree radial orientation difference) on the same sliding axis 1754. The configuration of the inner frames 1704 depicted in FIGS. 17A-17B, and other configurations in which the inner frames 1704 are each nested or otherwise disposed within a singular half 1716A, 1716B of the medial body 1716, may be preferred over the alternative configuration. Said adapter 1715 configuration of 17A-17B may keep the syringe flanges sufficiently far away from the adjoining association points between the two halve 1716A, 1716B to ensure that the manipulation of the syringe flanges 1703 does not risk opening the adapter 1715 during use, as a result of the force applied to the syringe flanges 1703. Additionally, the absence of inner frames 1704 between the halves 1716A, 1716B of the medial body 1716 results in a larger contact area between the two halves 1716A, 1716B, facilitating a more secure association that may use a greater quantity or larger size of hinges, attachment mechanism, etc.

Figures 18A, 18B:
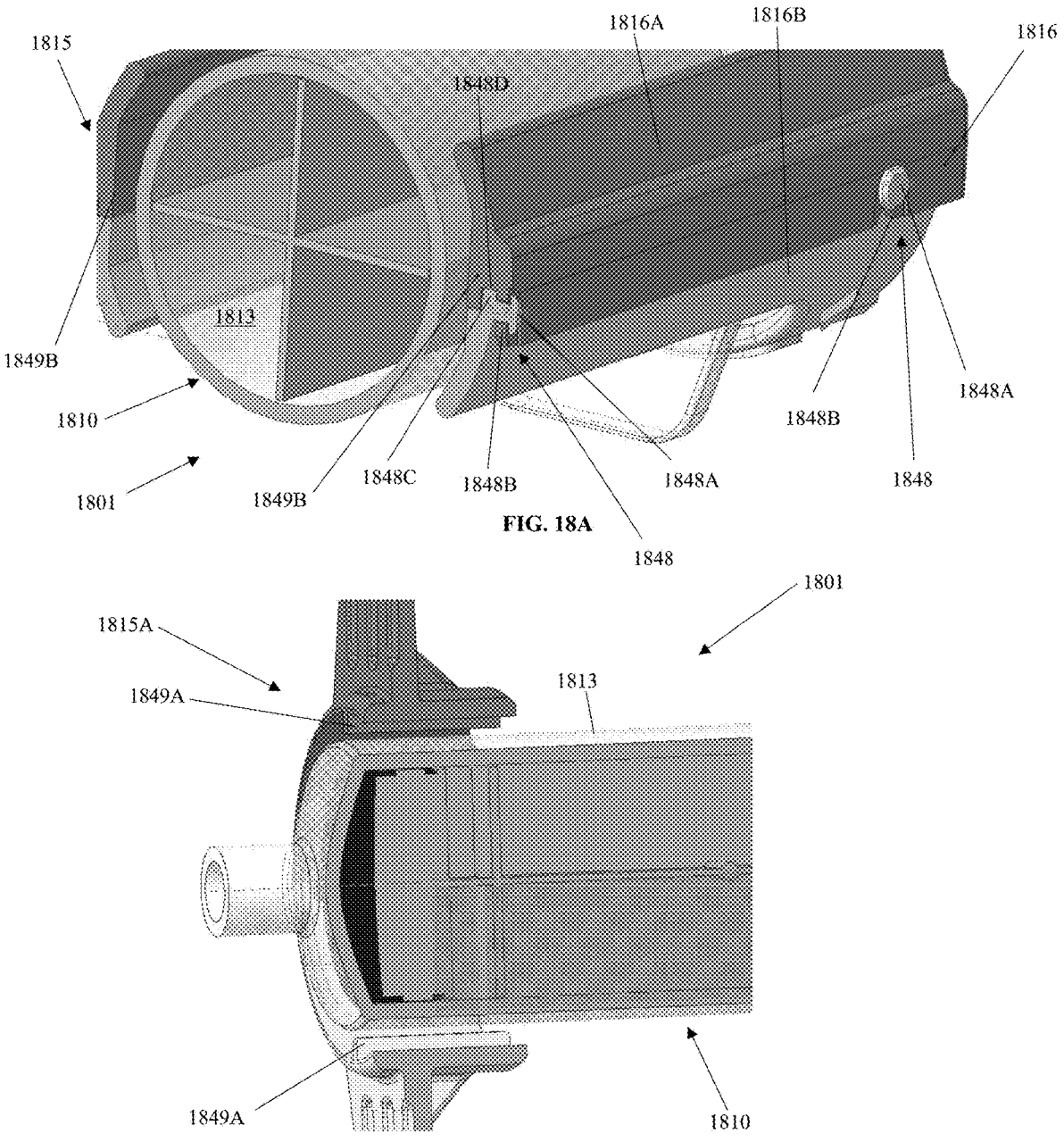
FIG. 18A-18B illustrate radial and longitudinal cross-section views of the blood drawing apparatus of FIG. 17B, in a closed state, respectively, according to an aspect

FIG. 18A-18B illustrate radial and longitudinal cross-section views of the blood drawing apparatus 1701 of FIG. 17B, in a closed state, respectively, according to an aspect. The structural details of the various components of the hereinabove disclosed knob lock 1848 may be seen in greater detail herein. As can be seen in FIG. 18A, while the adapter 1815 is secured in the closed position, each securing knob 1848A associated with or secured to the second half

1816B of the adapter is configured to be seated within a corresponding locking pocket 1848B nested within the first half 1816A of the adapter 1815A. Additionally, while the disclosed adapter 1815 is secured in the closed position, a securing ridge 1848C secured to or associated with the second half 1816B of the adapter 1815 is configured to be engaged with or seated within a corresponding securing slot 1848D nested within the first half 1816A of the adapter 1815. The engagement of each securing knob 1848A with a corresponding locking pocket 1848B and simultaneous engagement of the securing ridge 1848C with the securing slot 1848D, allows the two halves 1816A, 1816B of the adapter 1815 to be selectively secured to each other quickly and easily. It should be understood that the positioning of each knob lock 1848 may be varied, as long as the securing knob 1848A and locking pocket 1848B are on opposite halves of the medial body, and the securing ridge 1848C and securing slot 1848D are on opposite halves of the medial body.

It should be understood that variations to the size, shape and quantities of the knob locks 1848 and their various components may be implemented as needed depending on the needs of the specific application. For example, the usage of a larger syringe may necessitate the utilization of additional knob locks 1848 disposed along the corresponding first and second halves 1816A, 1816B of the medial body 1816. In an alternative embodiment, the size and shape of the securing knob 1848A may be modified in order make them easier to manipulate, by making the size of the securing knob larger, for example. The quantity and positioning of the alignment fins 1849A and alignment plates 1849B may also be modified to achieve the desired balance barrel 1813 control while minimizing the amount of friction the barrel 1813 experiences as it travels.

In another alternative embodiment, the prior disclosed hinges, such as molded hinges 721 of FIG. 7A-7B, may be replaced with a second set of locking mechanisms or adapter locks, such as the knob locks 1748 of FIG. 17A-17B. In such a variation, the two halves 1816A, 1816B of the medial body may be separate while the adapter 1815 is in the unlocked position. Both sides of each body half 1816A, 1816B may be configured to associate with each other via a separate sets of locking mechanisms in order to slidably surround the syringe for usage. Other variations may be made to the disclosed adapter 1815, its locking mechanisms and its various other components while still remaining within the scope of the specification.

For the sake of simplification, structures with functional and/or structural similarities between the various articulated and potential embodiments of the hereinabove disclosed blood drawing apparats may be classified into a plurality of component subgroups. There may be four main subgroups that account for the major functional components of each disclosed adapter. Elements of these subgroups may be arranged in such a manner to achieve the desired blood/fluid drawing functionality as described herein. For example, an adapter may be comprised of a barrel guide configured to movably surround the barrel, a plunger lock configured to secure the plunger to the adapter, a support body disposed between and associated with the barrel guide and the plunger lock, and a front grip associated with the barrel guide.

The first main subgroup referred to as "barrel guides", may include the applicable components of each embodiment of each adapter that movably surround and help guide the barrel portion of a syringe as said syringe is used to draw in a fluid (e.g., the barrel portion is moved away from the plunger top/toward the first end of the adapter). In adapter embodiments that utilize a medial body structure, such as the adapter 801 of FIG. 8, the guiding collar 851, or a comparable structure of the similar adapter embodiments of FIGS. 3-8 and FIGS. 15-18B, may be identified as the barrel guide. In the alternative adapter embodiments that utilize a telescoping activations arm, such as adapters 1101,1201 of FIG. 11, 12, the front collars 1133, 1233, and their equivalent structures found in FIGS. 13, 14, may be identified as barrel guides.

The second main subgroup, referred to as "plunger locks", may include structures that allow for the plunger of a syringe to be locked into position within an adapter to allow the described compression force to manipulate the barrel of the syringe, resulting in fluids being drawn into the syringe. In adapter embodiments that utilize a medial body structure, such as the adapter 801 of FIG. 8, the plunger top restrictor 852, (e.g, the press fit configuration 822), or comparable structures of the similar adapter embodiments of FIGS. 3-8 and FIGS. 15-18B, may be identified as the plunger lock. In the alternative adapter embodiments that utilize telescoping activations arm, such as adapters 1101,1201 of FIG. 11, 12, the U-rings 1134, 1234, and their equivalent structures found in FIGS. 13, 14, may be identified as plunger locks.

The third main subgroup, referred to as "support bodies", may include structures that are disposed between and associated with a corresponding barrel guide and plunger lock, to keep them a fixed distance apart to conform to the size of a selected syringe. In adapter embodiments that utilize a medial body structure, such as the adapter 801 of FIG. 8, the body housing 853, or comparable structures of the similar adapter embodiments of FIGS. 3-8 and FIGS. 15-18B, may be identified as the support bodies. In the alternative adapter embodiments that utilize telescoping activations arm, such as adapters 1101,1201 of FIG. 11, 12, the telescoping activation arm 1125, 1225, and their equivalent structures found in FIGS. 13, 14, may be identified as support bodies.

The fourth and final main subgroup, referred to as a "front grip", may include structures that provide a gripping point to use in conjunction with the syringe flange(s) to slide the barrel to operate the blood drawing apparatus. In adapter embodiments that utilize a medial body structure, such as the adapter 801 of FIG. 8, the adapter flanges 819A, 819B, or comparable structures of the similar adapter embodiments of FIGS. 3-8 and FIGS. 15-18B, may be identified as the front grip. In the alternative adapter embodiments that utilize telescoping activations arm, such as adapters 1101,1201 of FIG. 11, 12, the circular grip 1132,1232, and their equivalent structures found in FIGS. 13, 14, may be identified as the front grip. As can be seen from the disclosed embodiments, the front grip may be associated with barrel guide to ensure proper positioning.

In applicable embodiments, the elements used to further secured or associate the two halves (e.g., halves 716A and 716B, halves 816A and 816B, etc.) in conjunction with the prior described hinges, including snap locks 824 and 1335 of FIG. 8 and FIG. 13, respectively, the snap hooks 1542 and locking slots 1542 of FIG. 15, the knob locks 1748, 1848 of FIGS. 17A-18B, and every other hereinabove element that is configured to reversibly associate the two halves of the medial body, may all be classified as an adapter locks ("locking mechanisms")

As described hereinabove, when describing the compressive force utilized to draw fluids into the syringe, multiple phrases may be utilized to describe the same action. For example, moving the pair of syringe flanges 1803 toward the barrel guide should be understood as the same action as moving the pair of syringe flanges 1803 toward the adapter flanges 1819A/1819B or the front grip, as a result of causing the same result (e.g., sliding movement of the barrel through the barrel guide/front end 1815A). A phrase describing a compression force being applied "simultaneously" to the outer attachment flanges 1819 and the syringe flanges, or simply compressing the attachment flanges 1819 (e.g., the front grip) and the syringe flanges toward each other, also describe the same action disclosed hereinabove, wherein the barrel traverses forward through the first end 1815A of the adapter 1815. It should be understood, that the herein disclosed phrases utilized throughout the embodiments to describe this action may be considered equivalent when describing the operation of the disclosed blood drawing apparatus 1801.

It may be advantageous to set forth definitions of certain words and phrases used in this patent document. The term "couple" and its derivatives refer to any direct or indirect communication between two or more elements, whether or not those elements are in physical contact with one another. The term "or" is inclusive, meaning and/or. As used in this application, "and/or" means that the listed items are alternatives, but the alternatives also include any combination of the listed items.

The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Further, as used in this application, "plurality" means two or more. A "set" of items may include one or more of such items. The terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases.

Throughout this description, the aspects, embodiments or examples shown should be considered as exemplars, rather than limitations on the apparatus or procedures disclosed. Although some of the examples may involve specific combinations of method acts or system elements, it should be understood that those acts and those elements may be combined in other ways to accomplish the same objectives.

As used throughout this disclosure above, the phrases "liquids," "bodily liquids," "fluids," and "bodily fluids" are used interchangeably.

Acts, elements and features discussed only in connection with one aspect, embodiment or example are not intended to be excluded from a similar role(s) in other aspects, embodiments or examples.

Aspects, embodiments or examples of the invention may be described as processes, which are usually depicted using a flowchart, a flow diagram, a structure diagram, or a block diagram. Although a flowchart may depict the operations as a sequential process, many of the operations can be performed in parallel or concurrently. In addition, the order of the operations may be re-arranged. With regard to flowcharts, it should be understood that additional and fewer steps may be taken, and the steps as shown may be combined or further refined to achieve the described methods.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the invention. Therefore, the scope of this application is intended to cover such alternate aspects, embodiments and/or examples.

What is claimed is:

1. An adapter for a syringe having a barrel, a pair of syringe flanges secured to the barrel, and a plunger with a plunger top, the plunger being slidably disposed within the barrel, the adapter comprising:
    a barrel guide configured to movably surround the barrel;
    a plunger lock configured to secure the plunger to the adapter; and
    a support body disposed between and associated with the barrel guide and the plunger lock, the support body comprising a medial body having a first half and a second half joined by a hinge;
    an adapter lock configured to selectively secure the first half and the second half of the medial body together to surround the syringe within the adapter; and
    a front grip associated with the barrel guide;
    wherein application of a force to move the pair of syringe flanges toward the barrel guide is configured to cause the barrel to traverse forward through the barrel guide, thus causing a fluid to be drawn into the barrel.

2. The adapter of claim 1, wherein the first and second halves of the medial body are identical.

3. The adapter of claim 2, wherein the adapter lock is comprised of a knob lock having a locking pocket and a securing slot nested within the first half and a securing knob and a securing ridge secured to second half, wherein the securing knob and securing ridge are configured to be engaged with the locking pocket and the securing slot, respectively.

4. The adapter of claim 3, wherein the front grip is comprised of pair of adapter flanges associated to the barrel guide.

5. The adapter of claim 4, wherein the medial body further comprises a pair of inner frames, each inner frame of the pair of inner frames being nested within a different half of the medial body, wherein each inner frame of the pair of inner frames is configured to encircle and surround a corresponding syringe flange.

6. An adapter for a syringe having a barrel, a pair of syringe flanges secured to the barrel, and a plunger with a plunger top, the plunger being slidably disposed within the barrel, the adapter comprising:
    a barrel guide configured to movably surround the barrel;
    a plunger lock configured to secure the plunger to the adapter; and
    a support body disposed between and associated with the barrel guide and the plunger lock, the support body comprising a telescoping activation arm, the telescoping activation arm having a brace and a telescoping arm slidably connected to the brace, wherein the telescoping arm is configured to be selectively extended to modify a length of the telescoping activation arm to allow the adapter to secure a selected syringe; and
    a front grip associated with the barrel guide;
    wherein application of a force to move the pair of syringe flanges toward the barrel guide is configured to cause the barrel to traverse forward through the barrel guide, thus causing a fluid to be drawn into the barrel.

7. The adapter of claim 6, wherein the front grip comprises a circular grip.

8. The adapter of claim 7, wherein the barrel guide is comprised of a front collar.

9. The adapter of claim 8, wherein the plunger lock is comprised of a U-ring.

10. The adapter of claim 9, wherein the telescoping arm is configured to be adjusted through the selective engagement of at least one notch associated with the telescoping arm with a selected slot nested within the brace.

* * * * *